(12) United States Patent
Dott et al.

(10) Patent No.: US 8,785,435 B2
(45) Date of Patent: Jul. 22, 2014

(54) SOLID FORMS

(71) Applicant: Hoffmann-La Roche Inc., Nutley, NJ (US)

(72) Inventors: Pascal Dott, Rixheim (FR); Olaf Grassmann, Loerrach (DE); Michael Kammerer, Basel (CH); Joachim Manns, Fruthwilen (CH); Urs Schwitter, Reinach (CH); Andrew Thomas, Binningen (CH); Nicole Wyttenbach, Sissach (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 41 days.

(21) Appl. No.: 13/650,159

(22) Filed: Oct. 12, 2012

(65) Prior Publication Data

US 2013/0172329 A1 Jul. 4, 2013

(30) Foreign Application Priority Data

Oct. 20, 2011 (EP) .................................... 11185993

(51) Int. Cl.
*C07D 413/12* (2006.01)
*C07D 417/14* (2006.01)

(52) U.S. Cl.
USPC ..................................... 514/227.8; 544/58.2

(58) Field of Classification Search
CPC ..................................................... C07D 413/12
USPC ..................................... 544/58.2; 514/227.8
See application file for complete search history.

(56) References Cited

U.S. PATENT DOCUMENTS

| | | | |
|---|---|---|---|
| 4,639,266 A | 1/1987 | Heubach et al. | |
| 2003/0055085 A1 | 3/2003 | Wagener et al. | |
| 2004/0006226 A1 | 1/2004 | Ladduwahetty et al. | |
| 2009/0143371 A1 | 6/2009 | Buettelmann et al. | |
| 2009/0143407 A1 | 6/2009 | Buettelmann et al. | |
| 2010/0144744 A1 | 6/2010 | Li et al. | |

FOREIGN PATENT DOCUMENTS

| | | |
|---|---|---|
| DE | 352505 | 3/1986 |
| EP | 1894924 | 3/2008 |
| GB | 2336589 | 10/1999 |
| JP | 2007/230909 | 9/2007 |
| WO | 00/08001 | 2/2000 |
| WO | 00/77008 | 12/2000 |
| WO | 01/29015 | 4/2001 |
| WO | 01/34603 | 5/2001 |
| WO | 02/50062 | 6/2002 |
| WO | 02/081474 | 10/2002 |
| WO | 03/004027 | 1/2003 |
| WO | 03/015771 | 2/2003 |
| WO | 03/044017 | 5/2003 |
| WO | 03/048132 | 6/2003 |
| WO | 2004/048349 | 6/2004 |
| WO | 2005/014553 | 2/2005 |
| WO | 2005/113519 | 12/2005 |
| WO | 2005/118568 | 12/2005 |
| WO | 2005/123672 | 12/2005 |
| WO | 2006/037480 | 4/2006 |
| WO | 2006/044617 | 4/2006 |
| WO | 2006/069155 | 6/2006 |
| WO | 2006/095822 | 9/2006 |
| WO | 2007/002635 | 1/2007 |
| WO | 2007/009275 | 1/2007 |
| WO | 2007/039389 | 4/2007 |
| WO | 2007/042420 | 4/2007 |
| WO | 2007/052843 | 5/2007 |
| WO | WO 2007071476 A1 * | 6/2007 |
| WO | 2007/076260 | 7/2007 |
| WO | 2007/092751 | 8/2007 |
| WO | 2007/137954 | 12/2007 |
| WO | 2008/025539 | 3/2008 |
| WO | 2008/025540 | 3/2008 |
| WO | 2009/071476 | 6/2009 |

OTHER PUBLICATIONS

Cui et al., "Cell" 135:549-560 ( 2008).
Felix et al., Journal of Organic Chemistry 60:3907-3909 ( 1995).
Waldo et al., Organic Letters 7:5203-5205 ( 2005).
Ley et al., Angew Chem 115:5558-5606 ( 2003).
Amidon et al., Pharmaceutical Research (XP009035978), 12(3):413-420 (Jan. 1, 1995).
Papadimitriou, G. et al., Neuropsychobiology 43(3):141-144 ( 2001).
Wang et al., Journal of Fluorine Chemistry 111(2):241-246 ( 2001).
Andosova et al., Pharmaceutical Chemistry Journal 12(8):1019-1022 ( 1978).
White et al., Journal of Organic Chemistry 46(11):2273-2280 ( 1981).
Yu, Advanced Drug Delivery Systems (XP00905056), 48(1):27-42 (May 16, 2001).
(Translation of Jap Off Act in Corres Jap App 2010-536410 Oct. 30, 2012).

(Continued)

*Primary Examiner* — Kahsay Habte

(57) ABSTRACT

The instant invention relates to novel solid forms of the compound of formula (I)

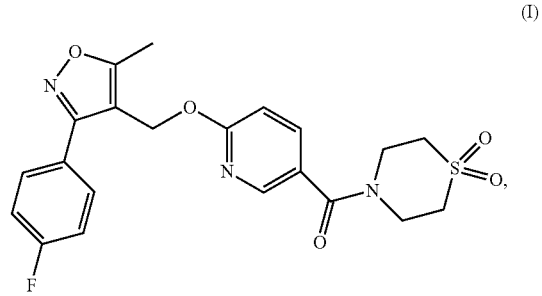

(I)

as well as solvates, inclusion complexes with other suitable compounds, processes for their manufacture, pharmaceutical compositions containing these solid forms, and their use as pharmaceuticals.

8 Claims, 23 Drawing Sheets

(56) References Cited

OTHER PUBLICATIONS

Deshayes et al., Synthesis:868-870 ( 1984).
Hancock, Journal of Pharmaceutical Sciences (XP000929450), 86(1):1-12 (Jan. 1, 1997).
Austin, William et al., J.Org. Chem. 46:2280-2286 (Nov. 1981).
Burke et al., Journal of Natural Products 49:522-523 ( 1986).
Fernandez et al., Nature Neuroscience 10(4):411-413 (Apr. 2007).
Bourbeau et al., Organic Letters 8(17):3679-3680 ( 2006).
Doyle et al., Journal of the Chemical Society:5838-5845 ( 1963).
Byrn et al., Pharmaceutical Research (XP000996386), 12(7):945-954 (Jul. 1, 1995).
Delong, R., "Autism" 11(2):135-147 ( 2007).
Hormi, Organic Syntheses 8 & 66:247, 173 ( 1993/1988).
Huettel et al., Liebigs, Ann. Chem. (eng. trans), 593:200-207 ( 1955).
Kumar et al., Tetrahedron Letters 47:1457-1460 ( 2006).
Otani et al., "Neuroscience Letters" 381:108-113 ( 2005).
Khankari et al., Thermochimica Acta (XP001162001), 248:61-79 (Jan. 1, 1995).
Anderson et al., Journal of Organic Chemistry 51(6):945-947 ( 1986).
(International Search Report for PCT/EP2012/070522 Feb. 7, 2013).
Roy et al., Synthesis:1347-1356 ( 2003).
McNamara et al., Psychobiology 21:101-108 ( 1993).
Schlosser et al., Eur. J. Org. Chem. 24:4181-4184 ( 2002).
Lam et al., Bioorganic & Medicinal Chemistry Letters 13(10):1795-1799 ( 2003).
Goodman et al., Tetrahedron 55:15067-15070 ( 1999).
XP055045886 retrieved from internet: http://www.sciencelb.com/msds.php?msdsId=9925323, pp. 1-6 (Material Safety Data Sheet for 2,2,2-Trifluroethanol Sep. 6, 2012).
Caira, Topics Curr. Chem. (XP001156954), 198:163-208 (Jan. 1, 1998).
Hamper et al., J. Agric. Food Chem. 43:219-228 ( 1995).
Kirk, K.L., Journal of Organic Chemistry 43:4381-4383 ( 1978).
Rueda et al., "Neuroscience Letters" 433:22-27 ( 2008).
Seydel et al., Journal of Medicinal Chemistry 19:483-492 ( 1976).
McCauley et al., "Amer. J. Med. Genetics" 131B:51-59 ( 2004).
Solis-Anez et al., "Investigacion Clinica" 48:529-541 ( 2007).
Shi Shun et al., Journal of Organic Chemistry 68:6810-6813 ( 2003).
Brewster et al., Advanced Drug Delivery Reviews (XP022211985), 59(7):645-666 (Aug. 24, 2007).
Craig et al., International Journal of Pharmaceutics (XP009100532), 179(2):179-207 (Mar. 15, 1999).
(Translation of Korean Off Act in Corres Korean Appl 20117019615 Dec. 20, 2012).

\* cited by examiner

Figure 23

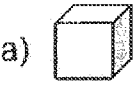 a) Equant crystals are equi-dimensional (like cubes or spheres);

 b) Plates are flat, tabular crystals and have a similar breath and width; thicker than flakes;

 c) Flakes are thin, flat crystals that have a similar breadth and width; thinner than plates;

 d) Blades (laths) are elongated, thin and blade-like crystals;

 e) Needles are acicular, thin and highly elongated crystals having similar width and breadth;

 f) Columns are elongated, prismatic crystals with greater width and thickness than needles.

SOLID FORMS

PRIORITY TO RELATED APPLICATION(S)

This application claims the benefit of European Patent Application No. 11185993.0, filed Oct. 20, 2011, which is hereby incorporated by reference in its entirety.

BACKGROUND OF THE INVENTION

Polymorphism is the ability of a compound to crystallize as more than one distinct crystal species. Different polymorphic forms (or polymorphs) have different arrangements or conformations of the molecules in the crystal lattice. If a solid does not possess a distinguishable crystal lattice and the molecular arrangement of molecules is disordered, it is considered amorphous. The amorphous state is structurally similar to the liquid state [W. McCrone, *Phys. Chem. Org. Solid State* (1965) 2:725767].

Polymorphic forms of a drug substance can have different chemical, physical and physicotechnical properties. Differences can result from e.g. packing of molecules in the crystal structure (density, refractive index, conductivity, hygroscopicity), thermodynamic properties (melting point, heat capacity, vapor pressure, solubility), kinetic properties (dissolution rate, stability), surface properties (surface free energy, interfacial tension, shape, morphology), and mechanical properties (compatibility, tensile strength). These properties can have a direct effect on the ability to process and manufacture the active pharmaceutical ingredient (API) and the drug product. Polymorphism further has pharmacological implications due to altered solid state properties and suitability for a particular formulation. Thus, polymorphism of an API can affect the quality, safety, efficacy and developability of a drug product and is therefore of fundamental importance [D. Giron et al., *J. Therm. Anal. Cal.* (2004) 77:709].

In addition to polymorphic modifications, an API can be crystallized in different salt forms with an appropriate counterion. Similar to polymorphism, salt forms are varying from each other in the degree of solubility and many other physical and chemical factors, as denoted above. As compared to the free acid or free base of the API, an appropriate salt form might provide improved aqueous solubility, dissolution rate, hygroscopicity, chemical stability, melting point, or mechanical properties.

Solvates, also known as pseudopolymorphs, are crystal forms having either stoichiometric or nonstoichiometric amounts of a solvent incorporated in the crystal lattice. If the incorporated solvent is water, the solvate is commonly known as a hydrate.

Salts and inclusion complexes both are multicomponent systems. Salts are formed by ionic bonding interactions with complete proton transfer between acid and base whereas in inclusion complexes the molecules are neutral in the crystalline state and are connected mainly through hydrogen bonds or Van der Waals interactions [S. L. Morissette et al., *Adv. Drug Del. Rev.* (2004) 56:275-300].

Cyclodextrins are comprised of six, seven, or eight glucose units, respectively, and have hydrophilic cavity exteriors and hydrophobic cavity interiors [V. J. Stella et al., *Adv. Drug Del. Rev.* (2007) 59:677-694]. These properties are responsible for their aqueous solubility and ability to incorporate hydrophobic molecular moieties within their cavities. Cyclodextrins can be employed as inclusion complex formers for inclusion complexes with APIs, in which the API is trapped by a cavity of cyclodextrin molecules. It is reported in the literature that the crystal structures of cyclodextrin inclusion complexes are typically dominated by the spatial arrangement of the host molecules. Thereby the cyclodextrin may form a defined packing arrangement similar to a crystalline state, whereas the API does not occupy well defined lattice positions [T. Uyar et al., *Cryst. Growth Des.* (2006) 6:1113-1119, T. Toropainen et al., *Pharm. Res.* (2007) 24:1058-1066].

Among the commercially available cyclodextrins, γ-cyclodextrin (γ-CD) is reported to be stable and has been found safe for oral administration [I. C. Munro et al., *Regulatory Toxicology and Pharmacology* (2004) 39:53-513]. However, γ-cyclodextrins are not used in marketed drug preparations up to now. A monograph has only recently (12/2008) been included in the European pharmacopoeia. The formation of inclusion complexes with cyclodextrins is not predictable and needs comprehensive experimental investigation. In those cases where inclusion complexes with γ-cyclodextrin are formed, most active pharmaceutical ingredients form a 2:1 complex (ratio between inclusion complex former and API). The formation of cyclodextrin inclusion complexes and their guest to host stoichiometries are highly dependent on the molecular structures and the geometrical sizes of the guest molecules [T. Uyar et al., *Cryst. Growth Des.* (2006) 6:1113-1119].

The compound of formula (I), its manufacture, its pharmacological activity as inverse agonists of the GABA A α5 receptor, and its use for the treatment, prevention and/or delay of progression of various central nervous system (CNS) conditions have been described in WO 2009/071476. Based on its physicochemical properties, the compound of formula (I), as described in WO 2009/071476, is a BCS 2 compound, exhibiting low aqueous solubility and high permeability, according to the biopharmaceutical classification system [G. L. Amidon, H. Lennernas, V. P. Shah, J. R. Crison, *Pharm. Res.* (1995) 12:413-420]. Hence the limited oral bioavailability is a major issue for oral formulation development.

If anhydrous solid forms of the compound of formula (I), as described in WO 2009/071476, are selected for clinical development, a physical instability in terms of hydrate formation during pharmaceutical processing and/or storage of the drug product is possible. Anhydrous solid form A of the compound of formula (I) as described in WO 2009/071476 and herein, has further been found to be only metastable and hence may convert into different solid forms. Hence there is a need to find new solid forms which feature enhanced physicochemical properties and improved bioavailability.

Further, the discovery of new solid forms of an API (polymorphs, solvates, salts, inclusion complexes) enlarges the repertoire of materials that a formulation scientist has available with which to design a pharmaceutical dosage form of a drug with a targeted release profile or other desired characteristics. Therefore, there is a need to find more solid forms of the compound of formula (I).

SUMMARY OF THE INVENTION

The instant invention provides novel solid forms of compounds of formula (I)

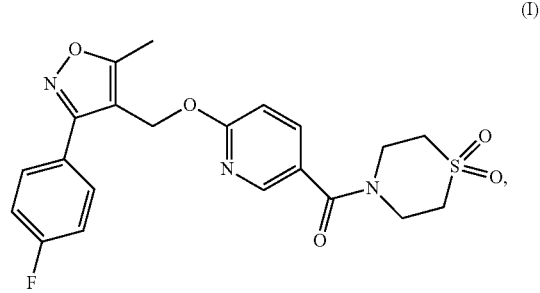 [SMILES: Cc1onc(-c2ccc(F)cc2)c1COc1ccc(C(=O)N2CCS(=O)(=O)CC2)cn1]

as well as their solvates, inclusion complexes with other suitable compounds, solvates of their inclusion complexes with other suitable compounds, processes for their manufacture, pharmaceutical compositions containing these solid forms, and their use as pharmaceuticals.

Under certain conditions new solid forms, particularly crystalline or amorphous forms, most particularly crystalline forms, of the compound of formula (I) can be obtained, which are described hereinafter, which have advantageous utilities and properties. They exhibit substantially different and superior physical and physicochemical properties which can be beneficial in various aspects relevant in API and drug product development, e.g. for dissolution of API, stability and shelf live of API and drug product, and/or facilitated routes of manufacturing or purification. The instant invention provides novel solid forms of the compound of formula (I) with improved solubility, dissolution rate, oral bioavailability as well as increased stability of the API.

In addition, the instant invention provides novel inclusion complexes of compounds of formula (I) with cyclodextrins. Such inclusion complexes further feature improved dissolution rate and bioavailability.

The new solid forms as described herein are distinguishable by X-ray powder diffraction, crystal structure analysis, vibrational spectroscopy, magnetic resonance and mass spectroscopy, calorimetry, thermogravimetry, dynamic vapour sorption as well as by microscopy.

BRIEF DESCRIPTION OF THE DRAWINGS

FIG. 23 depicts various crystal habits and a description of their structure as distinguished in USP, General Chapter <776> (Optical Microscopy)].

DETAILED DESCRIPTION OF THE INVENTION

Figure 1:
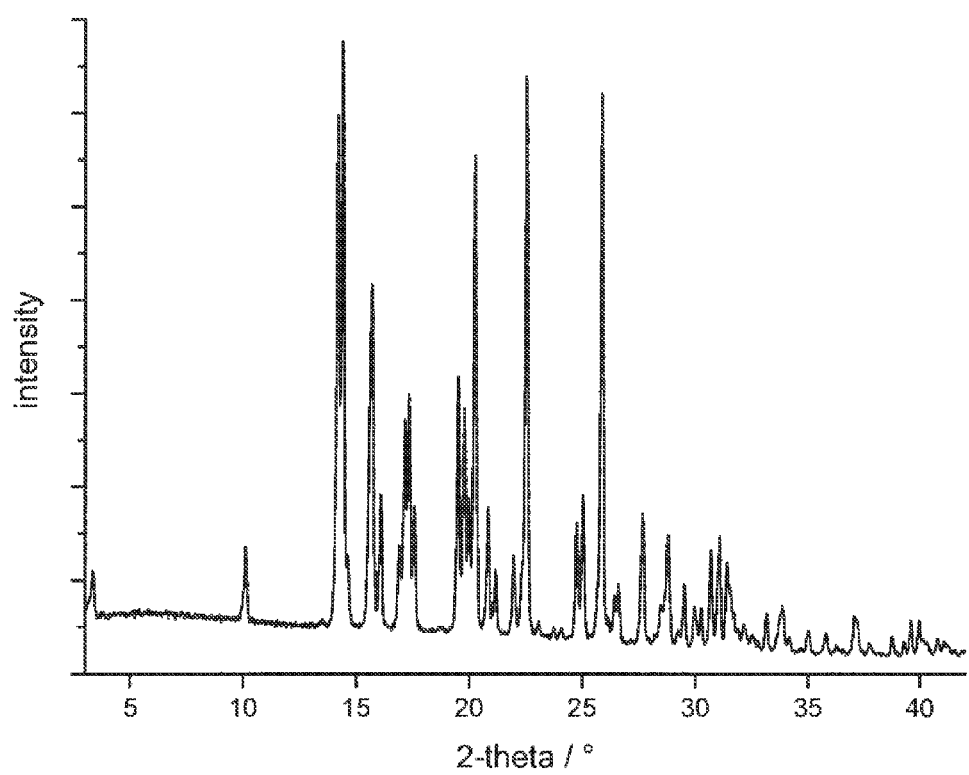
FIG. 1 depicts the XRPD pattern of Form A.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

Any open valency appearing on a carbon, oxygen, sulfur or nitrogen atom in the structures herein indicates the presence of a hydrogen atom, unless indicated otherwise.

The term "optional" or "optionally" denotes that a subsequently described event or circumstance may, but need not occur, and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogen atoms by substituents.

The term "halogen" denotes fluoro, chloro, bromo, or iodo. A particular halogen is fluoro.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl. A particular alkyl is methyl.

The term "alkoxy" denotes a group of the formula —O—R', wherein R' is an alkyl group as defined herein. Examples of alkoxy moieties include methoxy, ethoxy, isopropoxy, and tert-butoxy.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, and trifluoromethyl. The term "perhaloalkyl" denotes an alkyl group where all hydrogen atoms of the alkyl group have been replaced by the same or different halogen atoms.

The term "hydroxyalkyl" denotes an alkyl group wherein at least one of the hydrogen atoms of the alkyl group has been replaced by a hydroxy group. Examples of hydroxyalkyl include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl.

The term "heterocycloalkyl" denotes a monovalent saturated or partly unsaturated mono- or bicyclic ring system of 3 to 9 ring atoms, containing 1, 2, or 3 ring heteroatoms selected from N, O and S, the remaining ring atoms being carbon. In particular embodiments, heterocycloalkyl is a monovalent saturated monocyclic ring system of 4 to 7 ring atoms, containing 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, and 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, and dihydropyranyl. A particular heterocycloalkyl is (1,1-dioxo-1$\lambda^6$-thiomorpholin-4-yl).

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "aryl" denotes a monovalent aromatic carbocyclic mono- or bicyclic ring system containing 6 to 10 carbon ring atoms. Examples of aryl moieties include phenyl and naphthyl. A particular aryl is phenyl.

The term "heteroaryl" denotes a monovalent aromatic heterocyclic mono- or bicyclic ring system of 5 to 12 ring atoms, containing 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, and quinoxalinyl.

The term "active pharmaceutical ingredient" (or "API") denotes the compound in a pharmaceutical composition that has a particular biological activity.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

The term "solid form" or "form" is a general term to denote a crystal form and/or amorphous form of a solid material.

The terms "crystal form" and "crystalline form" can be used interchangeably to denote polymorphs and pseudo-polymorphs of a crystalline solid.

The terms "polymorph" and "modification" can be used synonymously to denote one particular crystal structure in which a compound can crystallize. Different polymorphs have different arrangements or conformations of the molecules in the crystal lattice but all share the same elemental composition.

The term "polymorphism" denotes the ability of a compound to form more than one polymorph.

The term "enantiotropy" denotes the relationship between two or more polymorphs of the same substance in which the rank order of thermodynamic stabilities of the polymorphs changes reversibly at a defined temperature.

The term "monotropy" denotes the relationship between two or more crystal forms of the same substance in which the rank order of thermodynamic stabilities of the polymorphs is retained at all temperatures below the melting point. A "metastable" form is a crystal form which does not have the highest rank order of thermodynamic stability.

The terms "solvate" and "pseudo-polymorph" can be used synonymously to denote a crystal having either stoichiometric or nonstoichiometric amounts of a solvent incorporated in the crystal lattice. If the incorporated solvent is water, the solvate formed is a "hydrate". When the incorporated solvent is alcohol, the solvate formed is an "alcoholate".

The term "salt" denotes a material which is composed of two components, an acid and a base with a clearly defined stoichiometric ratio of the two salt formers. Salt crystals are formed by ionic bonding interactions with complete transfer of hydrogen ions between acid and base.

The term "crystal shape" denotes the basic body element(s) (polyhedron(s)) of which a single crystal is built up. The crystal shape is described by the Miller indices of the lattice planes of the polyhedron(s).

The term "crystal habit" denotes the crystal morphology and hence the physical appearance of a solid form. Variations of crystal habit are caused by different growth rates of lattice planes. Various habits are distinguished [USP, General Chapter <776> (Optical Microscopy)]: in FIG. 23.

The term "equivalent spherical diameter" (or ESD) of a non-spherical object, e.g. an irregularly-shaped particle, is the diameter of a sphere of equivalent volume.

The terms "d50 value" and "mass-median diameter" (or MMD) can be used interchangeably and denote the average particle size by mass, i.e. the average equivalent diameter of a particle, which is defined as the diameter where 50% (w) of the particles of the ensemble have a larger equivalent spherical diameter, and the other 50% (w) have a smaller equivalent spherical diameter.

The term "amorphous form" denotes a solid material which does not possess a distinguishable crystal lattice and the molecular arrangement of molecules lacks a long-range order. In particular, amorphous denotes a material that does not show a sharp Bragg diffraction peak. Bragg's law describes the diffraction of crystalline material with the equation "2d·sin(theta)=n·lambda", wherein "d" denotes perpendicular distance (in Angstroms) between pairs of adjacent planes in a crystal ("d-spacing"), "theta" denotes the Bragg angle, "lambda" denotes the wavelength and "n" is an integer. When Bragg's law is fulfilled, the reflected beams are in phase and interfere constructively so that Bragg diffraction peaks are observed in the X-ray diffraction pattern. At angles of incidence other than the Bragg angle, reflected beams are out of phase and destructive interference or cancellation occurs. Amorphous material does not satisfy Bragg's law and no sharp Bragg diffraction peaks are observed in the X-ray diffraction pattern. The XRPD pattern of an amorphous material is further characterized by one or more amorphous halos.

The term "inclusion complex" denotes a stoichiometric multicomponent complex. In contrast to salts, no or only partial proton transfer is expected in inclusion complexes. An inclusion complex can be an amorphous form or a crystalline form. Particularly, an inclusion complex is a crystalline form. Inclusion complex formers are solid at room temperature. Particular inclusion complex former is cyclodextrin, most particularly γ-cyclodextrin (γ-CD). Particularly the inclusion complex former is in crystalline state in the inclusion complex. Particularly, an inclusion complex is a stoichiometric 1:1 or a 2:1 inclusion complex (ratio between inclusion complex former and API). Most particularly, an inclusion complex is a stoichiometric 1:1 inclusion complex (ratio between inclusion complex former and API). Inclusion complexes can form solvates, hydrates and can exist as different polymorphic forms.

The term "Form A" as used herein denotes the crystalline anhydrous polymorphic form A of (1,1-dioxo-1λ$^6$-thiomorpholin-4-yl)-{6-[3-(4-fluoro-phenyl)-5-methyl-isoxazol-4-ylmethoxy]-pyridin-3-yl}-methanone.

The term "Form B" as used herein denotes the crystalline polymorphic form B of (1,1-dioxo-1λ$^6$-thiomorpholin-4-yl)-{6-[3-(4-fluoro-phenyl)-5-methyl-isoxazol-4-ylmethoxy]-pyridin-3-yl}-methanone monohydrate.

The term "Form C" as used herein denotes the crystalline anhydrous polymorphic form C of (1,1-dioxo-1%$^6$-thiomorpholin-4-yl)-{6-[3-(4-fluoro-phenyl)-5-methyl-isoxazol-4-ylmethoxy]-pyridin-3-yl}-methanone.

The term "Form D" as used herein denotes the crystalline polymorphic form D of (1,1-dioxo-1λ$^6$-thiomorpholin-4-yl)-{6-[3-(4-fluoro-phenyl)-5-methyl-isoxazol-4-ylmethoxy]-pyridin-3-yl}-methanone trifluoroethanol mono-solvate.

The term "Form E" as used herein denotes the anhydrous crystalline polymorphic form E of (1,1-dioxo-1%$^6$-thiomorpholin-4-yl)-{6-[3-(4-fluoro-phenyl)-5-methyl-isoxazol-4-ylmethoxy]-pyridin-3-yl}-methanone.

The term "Amorphous Form" as used herein denotes the amorphous form of (1,1-dioxo-1λ$^6$-thiomorpholin-4-yl)-{6-[3-(4-fluoro-phenyl)-5-methyl-isoxazol-4-ylmethoxy]-pyridin-3-yl}-methanone.

The term "γ-CD inclusion complex" as used herein denotes the crystalline 1:1 inclusion complex of (1,1-dioxo-1λ$^6$-thiomorpholin-4-yl)-{6-[3-(4-fluoro-phenyl)-5-methyl-isoxazol-4-ylmethoxy]-pyridin-3-yl}-methanone with γ-Cyclodextrin.

The term "XRPD" denotes the analytical method of X-Ray Powder Diffraction. XRPD patterns were recorded at ambient conditions in transmission geometry with a STOE STADI P diffractometer (Cu K alpha radiation source, primary monochromator, position sensitive detector, angular range 3° to 42° 2Theta, approximately 60 minutes total measurement time). The repeatability of the angular values is in the range of 2Theta±0.2°. The term "approximately" given in combination with an angular value denotes the repeatability which is in the range of 2Theta±0.2°. The samples were prepared and analyzed without further processing (e.g. grinding or sieving) of the substance. The relative XRPD peak intensity is dependent upon many factors such as structure factor, temperature factor, crystallinity, polarization factor, multiplicity, and Lorentz factor. Relative intensities may vary considerably from one measurement to another due to preferred orientation effects.

Humidity Controlled XRPD analyses were performed in reflection geometry with a Siemens D5000 Diffractometer (Cu radiation source, Ni K beta filter, Scintillation detector, angular range 3° to 42° 2Theta, approximately 180 minutes total measurement time per humidity level). The diffractometer is equipped with an MRI (Materials Research Instruments) humidity chamber. The humidity within the chamber is adjusted with an ANSYCO humidity controller (SYCOS H—HOT).

For single crystal structure analysis a single crystal sample was mounted in a nylon loop on a goniometer and measured at ambient conditions. Alternatively, the crystal was cooled in a nitrogen stream during measurement. Data were collected on a GEMINI R Ultra diffractometer from Oxford Diffraction. Cu-radiation of 1.54 Å wavelength was used for data collection. Data was processed with the Oxford Diffraction CRYSALIS software. The crystal structure was solved and refined with standard crystallographic software. In this case the program She1XTL from Bruker AXS (Karlsruhe) was used.

The abbreviation "FWHM" denotes the full width at half maximum, which is a width of a peak (e.g. appearing in a spectrum, particularly in an XRPD pattern) at its half height.

The term "sharp Bragg diffraction peak" in connection with X-ray diffraction patterns denotes a peak which is observed if Bragg's law of diffraction is fulfilled. Generally, the FWHM of a sharp Bragg diffraction peak is less than 0.5° 2-theta.

The term "amorphous halo" in connection with X-ray diffraction patterns denotes an approximately bell-shaped diffraction maximum in the X-ray powder diffraction pattern of an amorphous material. The FWHM of an amorphous halo is on principle larger than the FWHM of the peak of crystalline material.

The terms "FTIR" and "IR" denote the analytical method of infrared spectroscopy. The IR-spectra of the samples are recorded as film of a Nujol suspension consisting of approx. 5 mg of sample and approx. 5 mg of Nujol (mineral oil) between two sodium chloride plates (cross section 13 mm) in transmittance with a FTIR-spectrometer. The spectra were recorded in spectral range between 4000 cm$^{-1}$ and 600 cm$^{-1}$, resolution 2 cm$^{-1}$, and 300 coadded scans on a Magna 860 (thermo/Nicolet) equipped with a DTGS detector.

The term "Raman" denotes the analytical method of Raman spectroscopy. For recording Raman spectra, the samples were spread on a glass slide. Raman spectra were recorded in the range of 150-3800 cm$^{-1}$ with an ARAMIS (HoribaJobinYvon) Raman microscope equipped with a Peltier cooled CCD detector, at excitation of 633 nm, a 1200 Umm grating, a ×50 objective and with 3 exposures of 3 s, or 7 s for weak Raman scatterers.

The term "DSC" denotes the analytical method of Differential Scanning calorimetry. DSC thermograms were recorded using a Mettler-Toledo™ differential scanning calorimeter DSC820, DSC821 or DSC1 with a FRS05 sensor. System suitability tests were performed with Indium as reference substance and calibrations were carried out using Indium, Benzoic acid, Biphenyl and Zinc as reference substances.

For the measurements, approximately 2-6 mg of sample were placed in aluminum pans, accurately weighed and hermetically closed with perforation lids. Prior to measurement, the lids were automatically pierced resulting in approx. 1.5 mm pin holes. The samples were then heated under a flow of nitrogen of about 100 mL/min using heating rates of usually 10 K/min. For the measurements of amorphous forms, approximately 2-6 mg of sample were placed in aluminum pans, accurately weighed and hermetically closed. The samples were then heated under a flow of nitrogen of about 100 mL/min using heating rates of 10 K/min.

The term "onset" denotes the intersection point of the baseline before transition and the interflection tangent.

The term "glass transition temp" (Tg) denotes the temperature above which a glassy amorphous solid becomes rubbery.

The term "TGA" denotes the analytical method of Thermo Gravimetric Analysis. TGA analysis was performed on a Mettler-Toledo™ thermogravimetric analyzer (TGA850 or TGA851). System suitability tests were performed with Hydranal as reference substance and calibrations using Aluminum and Indium as reference substances.

For the thermogravimetric analyses, approx. 5-10 mg of sample were placed in aluminum pans, accurately weighed and hermetically closed with perforation lids. Prior to measurement, the lids were automatically pierced resulting in approx. 1.5 mm pin holes. The samples were then heated under a flow of nitrogen of about 50 mL/min using a heating rate of 5 K/min.

The term "micronization" denotes a process whereby the particle size of a solid material is diminished to a d50 value of less than 10 μm by the aid of a suitable method, such as milling, bashing or grinding.

The term "polishing filtration" denotes a filtration process wherein a solution is filtrated using a 0.2 μm filter, particularly a Pall N66 Posidyne® 0.2 μm filter cartridge, to remove fine particles.

The term "distillative solvent exchange" denotes a thermal distillation under reduced or normal pressure wherein one liquid (solvent or antisolvent) is replaced by another liquid (solvent or antisolvent), usually under constant reactor liquid level.

The term "solvent" denotes any kind of liquid in which the product is at least partially soluble (solubility of product >1 g/l).

The term "antisolvent" denotes any kind of liquid in which the product is insoluble or at maximum sparingly soluble (solubility of product <0.01 mol/l).

The term "anti-solvent crystallization" denotes a process wherein supersaturation and as a result thereof crystallisation is achieved by addition of an antisolvent to the product solution.

The term "ambient conditions" denotes conditions as experienced in a standard laboratory, e.g. atmospheric pressure, air, ambient temperature between 18° C. and 28° C., humidity between 30% rH and 80% rH.

The term "hygroscopicity" describes the ability of a solid material to adsorb moisture. The hygroscopicity of a given API is characterized [*European Pharmacopoeia*—6th Edition (2008), Chapter 5.11] by the increase in mass when the relative humidity is raised from 0% rH to 90% rH:

non-hygroscopic: weight increase $\Delta m<0.2\%$;
slightly hygroscopic: weight increase $0.2\%\leq\Delta m<2.0\%$;
hygroscopic: weight increase $2.0\%\leq\Delta m<15.0\%$;
very hygroscopic: weight increase $\Delta m\geq15.0\%$;
deliquescent: sufficient water is adsorbed to form a liquid.

The IUPAC lamda convention (W. H. Powell, *Pure & Appl. Chem.* (1984) 56(6): 769-778) provides a general method for indicating nonstandard valence states of heteroatoms in a molecule. The bonding number "n" of a heteroatom is the sum of the total number of valence bonds to adjacent atoms, if any, and the number of attached hydrogen atoms. The bonding number of a heteroatom is standard when it has the value given in the following table:

n=4: C, Si, Ge, Sn, Pb;
n=3: B, N, P, As, Sb, Bi;
n=2: O, S, Se, Te, Po;
n=1: F, Cl, Br, I, At.

A non-standard bonding number of a (neutral) heteroatom is indicated by the symbol "$\lambda^n$", where "n" is the bonding number. If the locant, the number indicating the position within the molecule, for a heteroatom with a nonstandard bonding number is used, the $\lambda^n$ symbol is cited immediately after this locant.

The terms (1,1-dioxo-1$\lambda^6$-thiomorpholin-4-yl)-, (1,1-dioxo-1λ6-thiomorpholin-4-yl)-, (1,1-dioxo-1λ6-thiomorpholin-4-yl)-, and (1,1-dioxo-thiomorpholin-4-yl)- are used herein interchangeably to denote a thiomorpholinyl-radical wherein the sulfur ringatom is substituted with two oxo groups of the structure as follows:

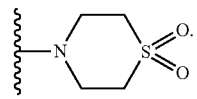

In detail, the present invention provides novel solid forms, particularly crystalline or amorphous forms, most particularly crystalline forms, of compounds of formula (I)

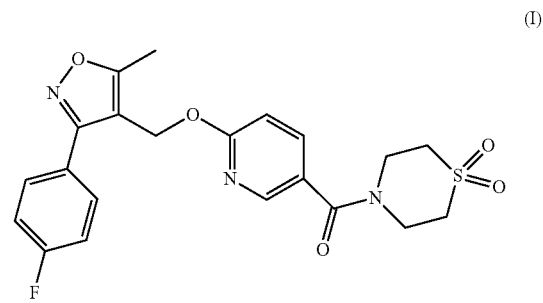 [SMILES: Cc1onc(-c2ccc(F)cc2)c1COc1ccc(C(=O)N2CCS(=O)(=O)CC2)cn1]

or a solvate thereof; or an inclusion complex thereof with one or more inclusion complex forming agents; or a solvate of an inclusion complex thereof with one or more inclusion complex forming agents.

(1,1-Dioxo-1$\lambda^6$-thiomorpholin-4-yl)-{6-[3-(4-fluoro-phenyl)-5-methyl-isoxazol-4-ylmethoxy]-pyridin-3-yl}-methanone [CAS No. 1159600-41-5] refers to the compound of formula (I) and vice versa.

In a particular embodiment, the invention provides solid forms of compounds of formula (I) as described above characterized by an XRPD pattern containing at least one XRPD peak in the range of angles of diffraction 2Theta of 10.3° to 13.3°.

In a particular embodiment, the invention provides solid forms of a compound of formula (I) as described above; or a solvate thereof; or an inclusion complex thereof with one or more inclusion complex forming agents; or a solvate of an inclusion complex thereof with one or more inclusion complex forming agents; characterized by an XRPD pattern containing at least one XRPD peak in the range of angles of diffraction 2Theta of 10.3° to 13.3°.

In a particular embodiment of the invention, the solid form of a compound of formula (I) as described above is a crystalline form.

In a particular embodiment of the invention, the solid form of a compound of formula (I) as described above is present in the specified solid form in a purity of at least 90% (w/w), particularly at least 95% (w/w), most particularly at least 99% (w/w).

(1,1-Dioxo-1λ$^6$-thiomorpholin-4-yl)-{6-[3-(4-fluoro-phenyl)-5-methyl-isoxazol-4-ylmethoxy]-pyridin-3-yl}-methanone in anhydrous polymorphic form A (Form A) has been described in WO 2009/071476.

Form A is a metastable polymorph with a melting temperature of approximately 145° C. (extrapol. peak DSC). Due to its metastable character Form A is not optimally suited for drug product development.

Form A is characterized by XRPD peaks at angles of diffraction 2Theta of 3.3°, 10.1°, 14.2°, 14.4°, 15.7°, 16.1°, 17.2°, 17.3°, 19.5°, 19.8°, 20.2°, 20.8°, 22.5°, 24.8°, 25.0°, 25.9°, 27.7°; particularly by XRPD peaks observed at an angle of diffraction 2Theta of 14.4°, 20.2°, 22.5°, 25.9°.

Form A is characterized by the XRPD diffraction pattern of FIG. 1.

Form A is characterized by an XRPD diffraction pattern containing XRPD peaks at peak positions as denoted in Table 2.

Figure 8:
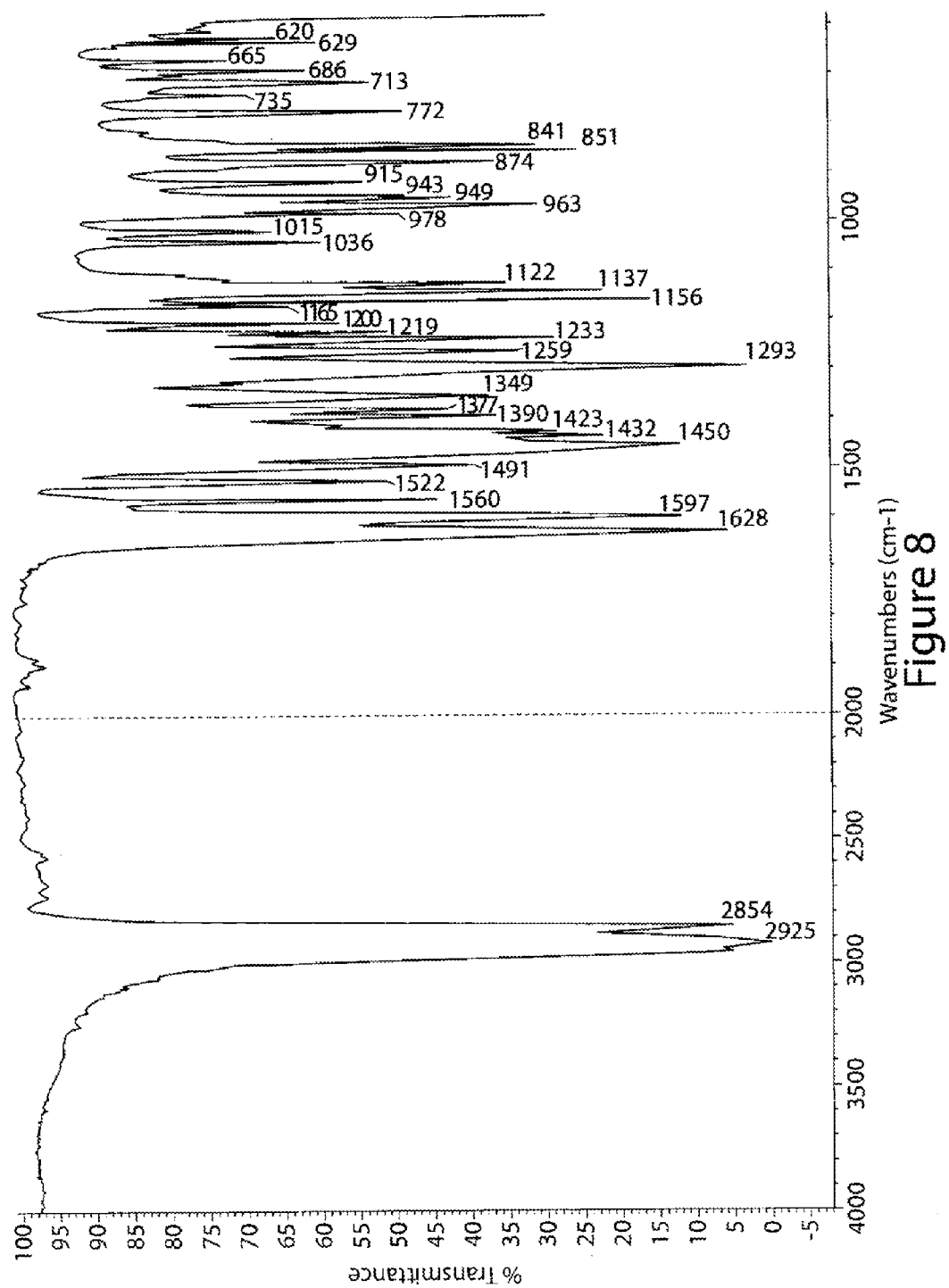
FIG. 8 depicts the FT-IR spectrum of Form A.
Figure 14:
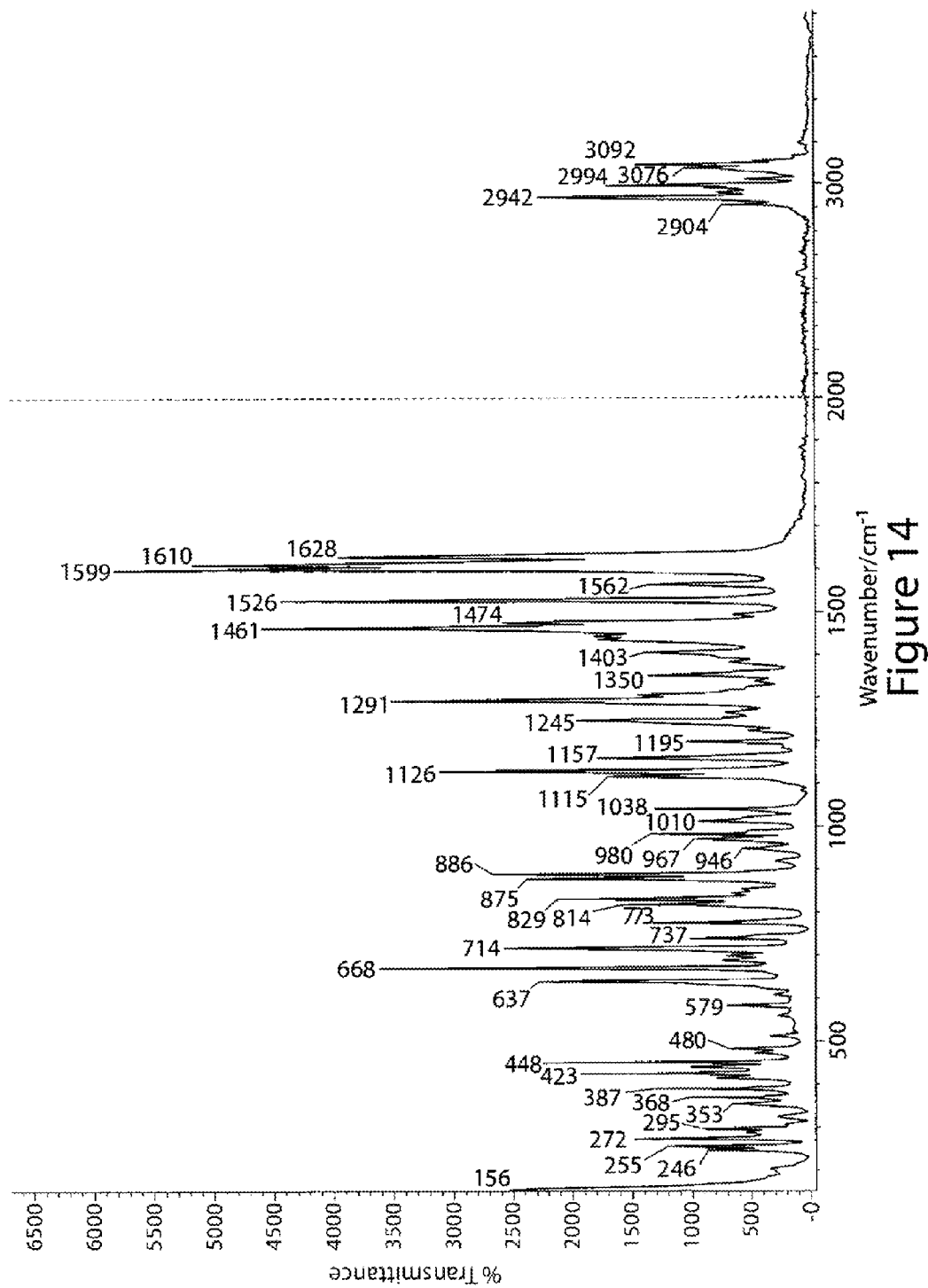
FIG. 14 depicts the Raman spectrum of Form A.

Form A is characterized by the FTIR spectrum of FIG. 8.
Form A is characterized by the Raman spectrum of FIG. 14.
Form A is characterized by a melting point with onset temperature (DSC) in the range of about 141° C. to 145° C.

(1,1-dioxo-1λ$^6$-thiomorpholin-4-yl)-{6-[3-(4-fluoro-phenyl)-5-methyl-isoxazol-4-ylmethoxy]-pyridin-3-yl}-methanone can be isolated, depending upon the method of preparation, in other different crystalline and amorphous modifications, which are distinguishable by their X-ray powder diffraction patterns, vibrational spectra and their melting behaviour and which exhibit surprising but relevant advantages beneficial for API and drug product development and administration as compared to previously described Form A.

Besides the previously described Form A of (1,1-dioxo-1λ$^6$-thiomorpholin-4-yl)-{6-[3-(4-fluoro-phenyl)-5-methyl-isoxazol-4-ylmethoxy]-pyridin-3-yl}-methanone, two further polymorphic anhydrous forms (Form C and Form E), one monohydrate form (Form B), a trifluoroethanol form (Form D), as well as an amorphous form were discovered and characterized.

Form B of (1,1-dioxo-1λ$^6$-thiomorpholin-4-yl)-{6-[3-(4-fluoro-phenyl)-5-methyl-isoxazol-4-ylmethoxy]-pyridin-3-yl}-methanone is a hygroscopic mono-hydrate that transforms into Form A upon heating to >100° C. Stability of Form B is substantially increased as compared to Form A in the presence of humidity, e.g. at ambient conditions.

Temperature Controlled XRPD analyses of Form B show a phase transition to Form A at elevated temperature. In the temperature range 105-135° C. only Form A is present. In the temperature range of 65-95° C. an intermediate state is observed that is characterized by significant changes in peak positions.

One particular embodiment of the invention provides crystalline (1,1-dioxo-1λ$^6$-thiomorpholin-4-yl)-{6-[3-(4-fluoro-phenyl)-5-methyl-isoxazol-4-ylmethoxy]-pyridin-3-yl}-methanone monohydrate in polymorphic form B (Form B) as described herein.

In a particular embodiment of the invention, Form B is characterized by an XRPD diffraction pattern containing XRPD peaks at angles of diffraction 2Theta of approximately 13.3°, 20.6°, 22.5°.

In a particular embodiment of the invention, Form B is characterized by an XRPD diffraction pattern containing XRPD peaks at angles of diffraction 2Theta of approximately 10.9°, 13.0°, 13.3°, 14.1°, 14.8°, 16.5°, 17.0°, 18.9°, 20.6°, 21.0°, 22.5°, 23.4°, 24.8°, 26.9°.

Figure 2:
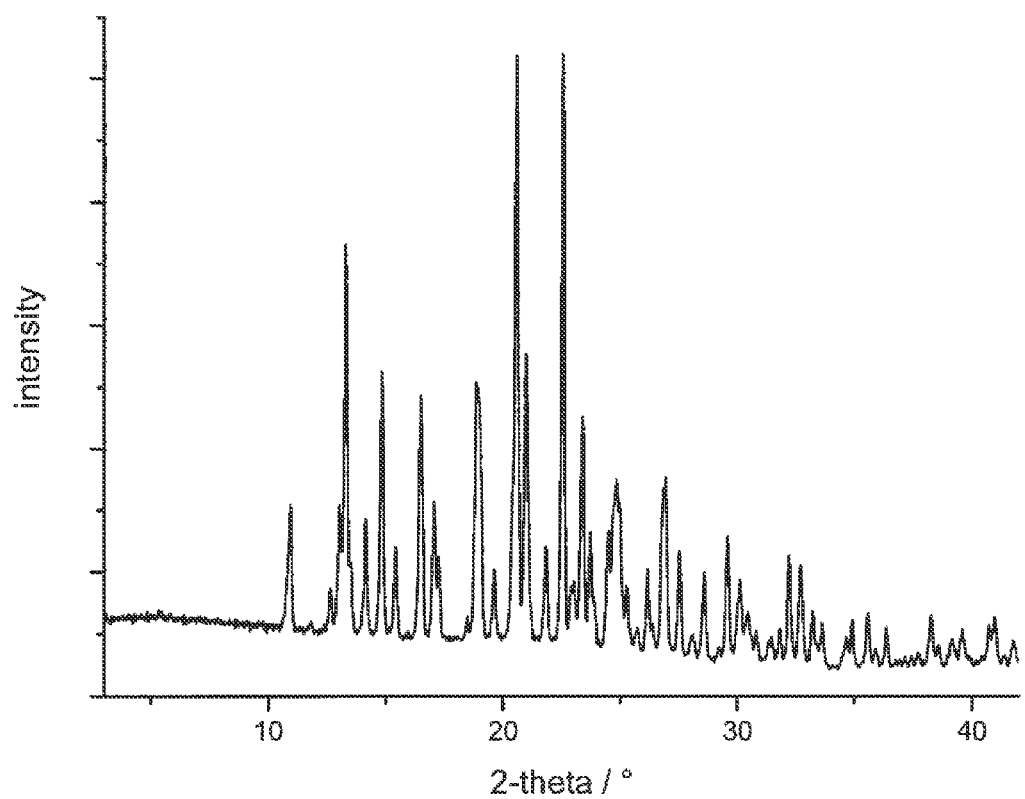
FIG. 2 depicts the XRPD pattern of Form B.

In a particular embodiment of the invention, Form B is characterized by the XRPD diffraction pattern of FIG. 2.

In a particular embodiment of the invention, Form B is characterized by an XRPD diffraction pattern containing XRPD peaks at peak positions as denoted in Table 3.

Figure 9:
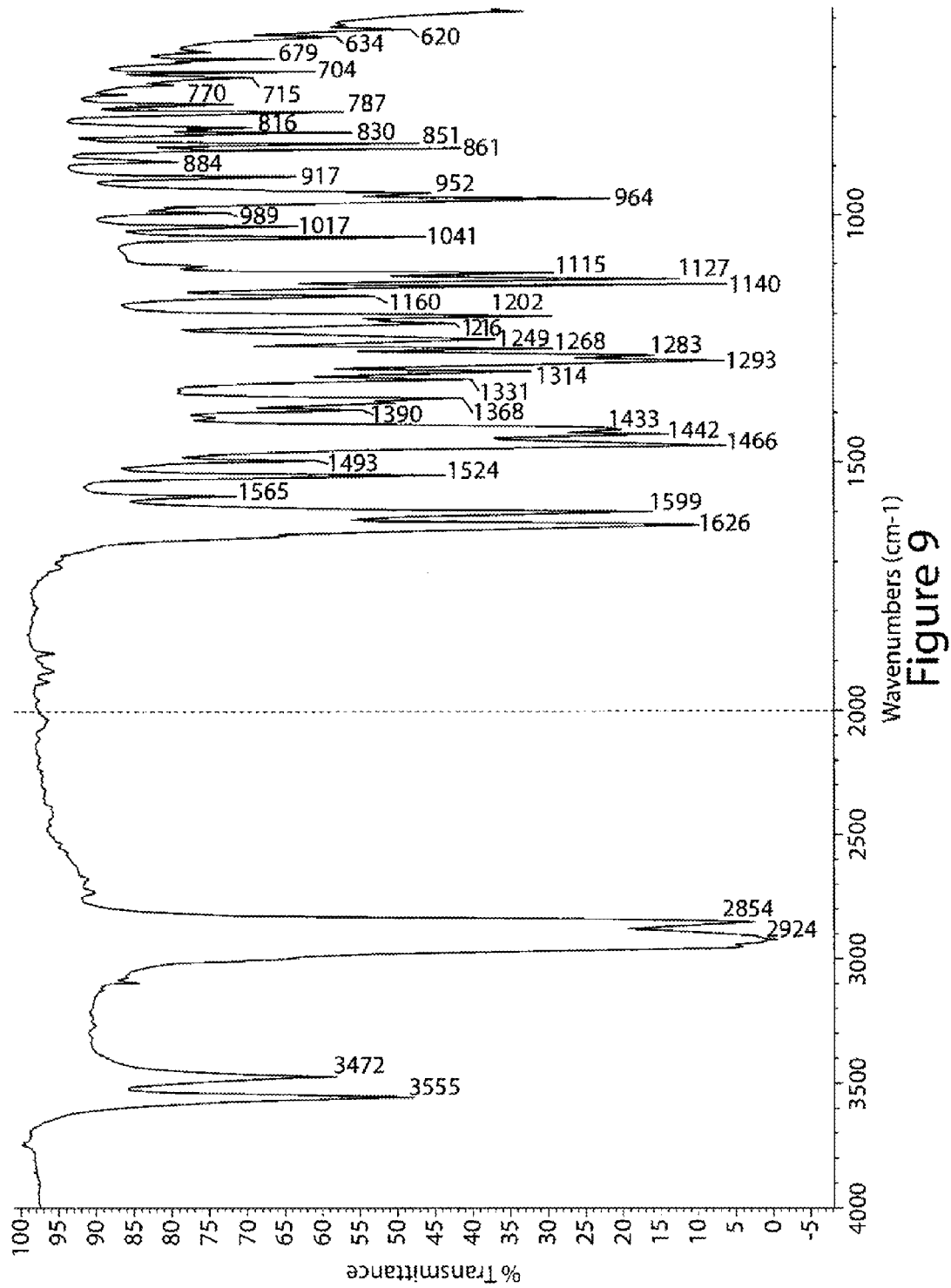
FIG. 9 depicts the FT-IR spectrum of Form B. In a particular embodiment of the invention, Form B is characterized by the FTIR spectrum of FIG. 9.

In a particular embodiment of the invention, Form B is characterized by the FTIR spectrum of FIG. 9.

Figure 15:
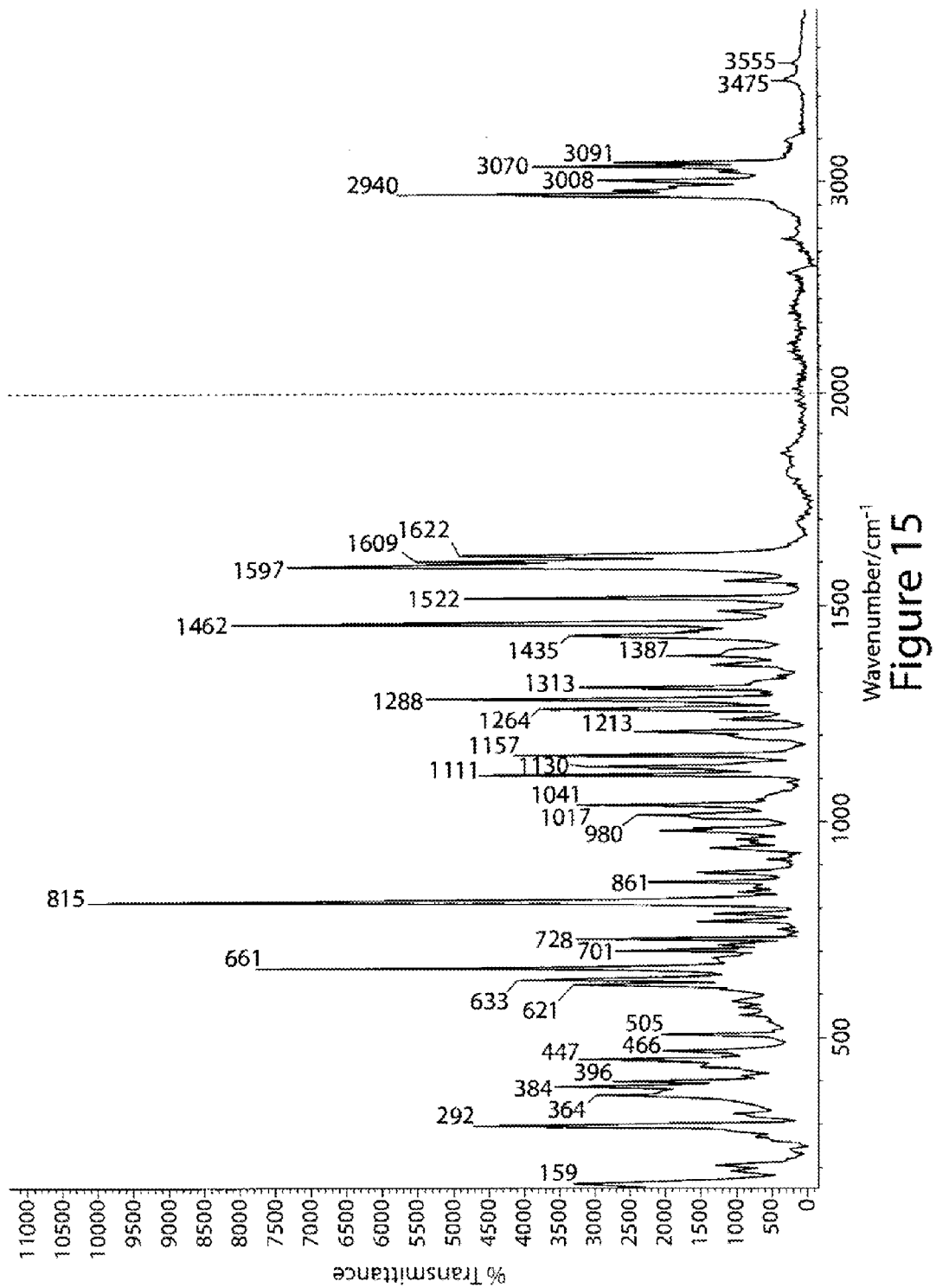
FIG. 15 depicts the Raman spectrum of Form B.

In a particular embodiment of the invention, Form B is characterized by the Raman spectrum of FIG. 15.

In a particular embodiment of the invention, Form B is characterized by a broad endothermic signal from 90° C. to 110° C. accompanied by weight loss (measured by TGA).

Form C of (1,1-dioxo-1λ$^6$-thiomorpholin-4-yl)-{6-[3-(4-fluoro-phenyl)-5-methyl-isoxazol-4-ylmethoxy]-pyridin-3-yl}-methanone is more stable than Form A. In fact, Form C is the most stable polymorph overall. Form C is in addition less hygroscopic than Form A and has a melting temperature of approx. 151° C. (extrapol. peak DSC). The solubility in simulated gastric fluid (SGF) of Form C is considerably improved as compared to Form B. In the presence of water, Form C transforms into Form B in suspended state, whereas storage at 100% rH at ambient temperature for a prolonged period of time, e.g. for 30 days does not induce this phase change.

Temperature Controlled XRPD analyses of polymorphs Form A and Form C do not show solid form changes at elevated temperature.

One particular embodiment of the invention provides crystalline (1,1-dioxo-1λ$^6$-thiomorpholin-4-yl)-{6-[3-(4-fluoro-phenyl)-5-methyl-isoxazol-4-ylmethoxy]-pyridin-3-yl}-methanone in anhydrous polymorphic form C (Form C) as described herein.

In a particular embodiment of the invention, Form C is characterized by an XRPD diffraction pattern containing XRPD peaks at angles of diffraction 2Theta of approximately 17.4°, 23.4°.

In a particular embodiment of the invention, Form C is characterized by an XRPD diffraction pattern containing XRPD peaks at angles of diffraction 2Theta of approximately 11.7°, 17.4°, 23.4°.

In a particular embodiment of the invention, Form C is characterized by an XRPD diffraction pattern containing XRPD peaks at angles of diffraction 2Theta of approximately 10.5°, 11.7°, 14.2°, 16.3°, 16.7°, 17.4°, 17.9°, 19.3°, 23.4°, 24.7°, 25.1°, 25.9°.

Figure 3:
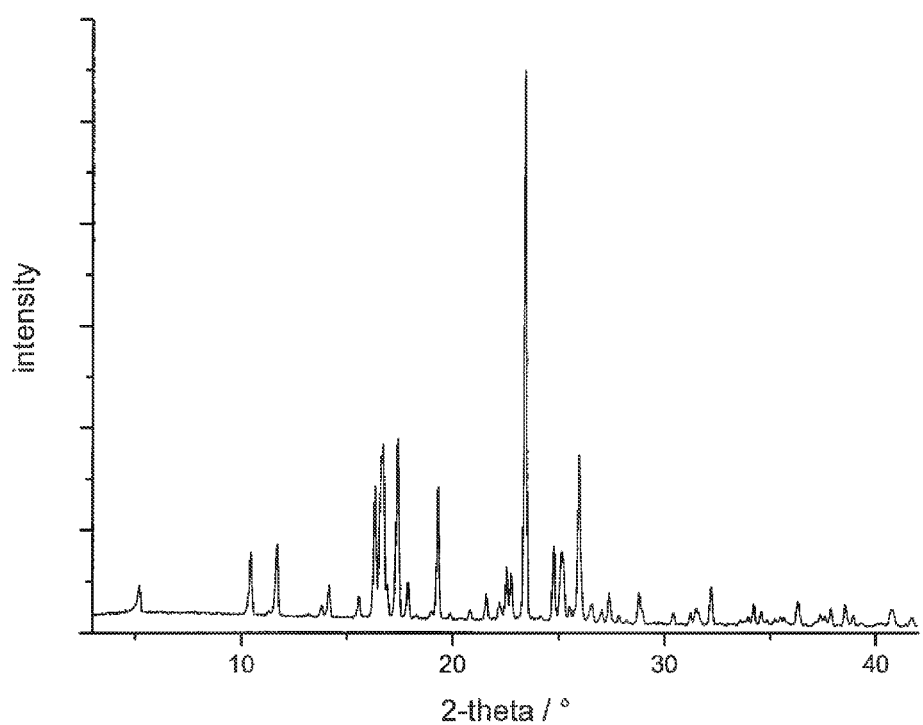
FIG. 3 depicts the XRPD pattern of Form C.

In a particular embodiment of the invention, Form C is characterized by the XRPD diffraction pattern of FIG. 3.

In a particular embodiment of the invention, Form C is characterized by an XRPD diffraction pattern containing XRPD peaks at peak positions as denoted in Table 4.

Figure 10:
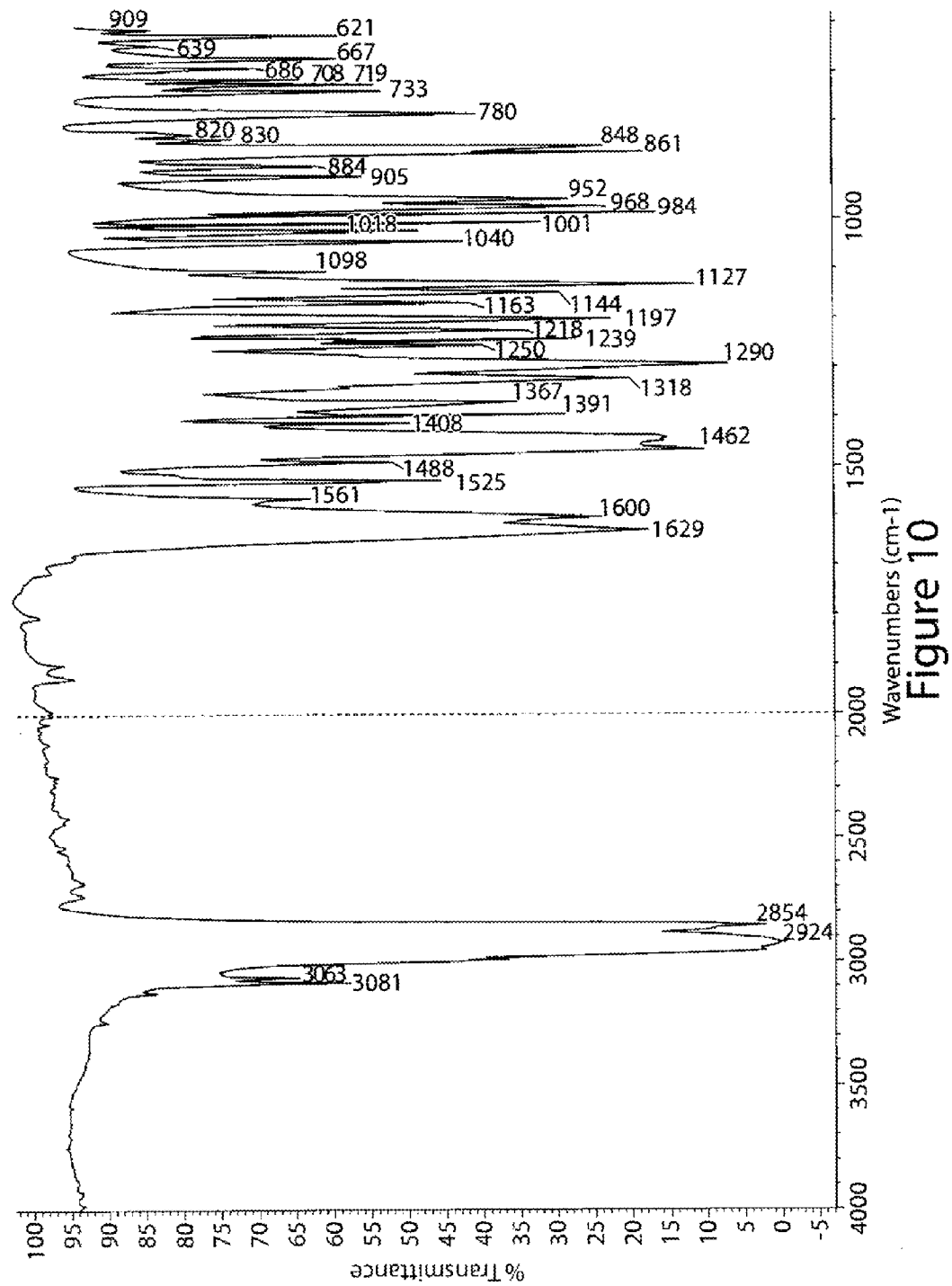
FIG. 10 depicts the FT-IR spectrum of Form C.

In a particular embodiment of the invention, Form C is characterized by the FTIR spectrum of FIG. 10.

Figure 16:
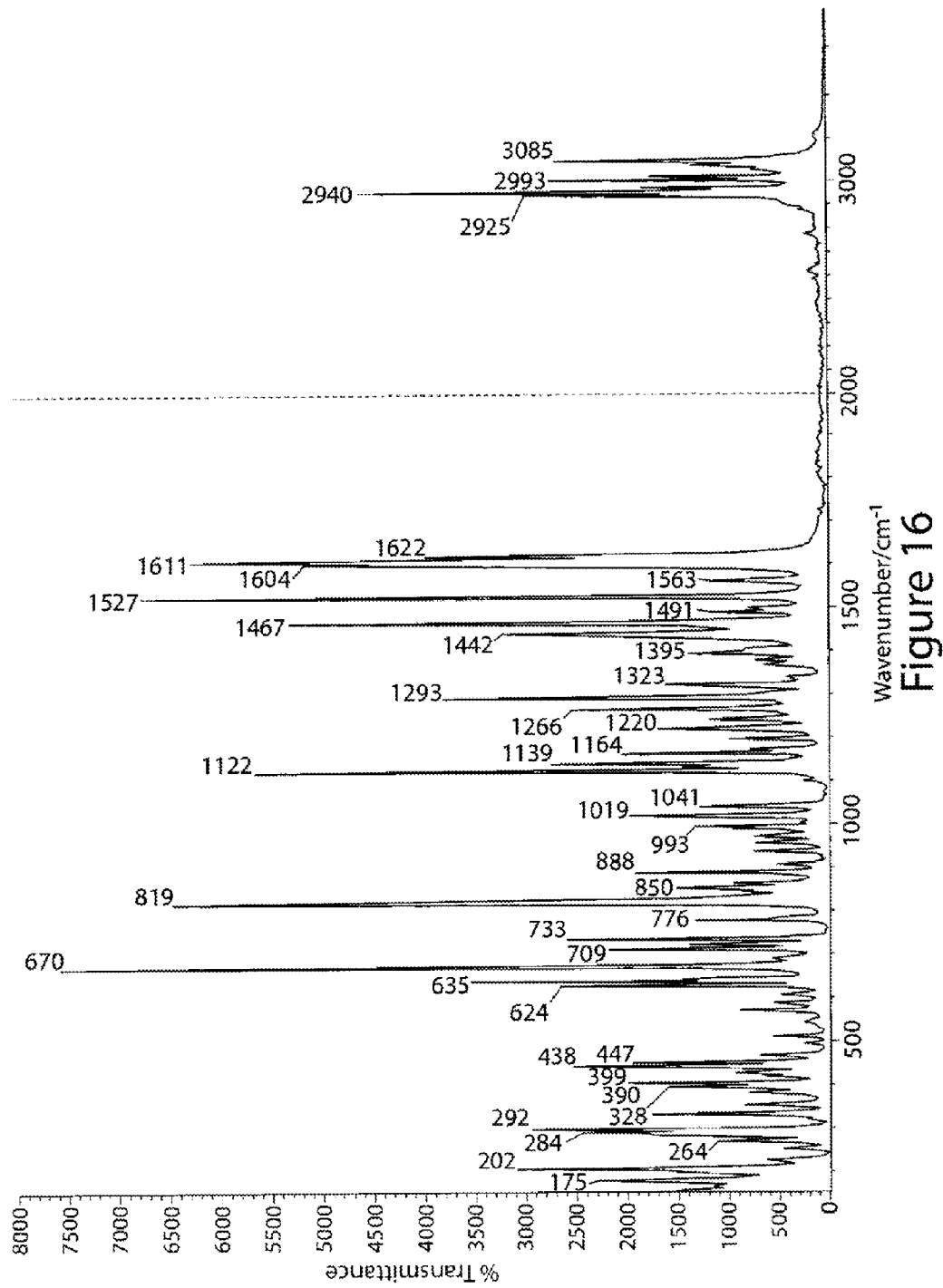
FIG. 16 depicts the Raman spectrum of Form C.

In a particular embodiment of the invention, Form C is characterized by the Raman spectrum of FIG. 16.

In a particular embodiment of the invention, Form C is characterized by a melting point with onset temperature (DSC) in the range of about 146° C. to 150° C.

Form D of (1,1-dioxo-1λ$^6$-thiomorpholin-4-yl)-{6-[3-(4-fluoro-phenyl)-5-methyl-isoxazol-4-ylmethoxy]-pyridin-3-yl}-methanone is a trifluoroethanol mono-solvate that can be generated by crystallization from trifluoroethanol/methanol mixtures. Form D is offers the benefit over Form A, that it is readily obtainable in case trifluoroethanol is employed in the manufacturing process.

One particular embodiment of the invention provides crystalline (1,1-dioxo-1λ$^6$-thiomorpholin-4-yl)-{6-[3-(4-fluoro-phenyl)-5-methyl-isoxazol-4-ylmethoxy]-pyridin-3-yl}-methanone trifluoroethanol mono-solvate in polymorphic form D (Form D) as described herein. Form D has a melting temperature of approx. 97.9° C. (extrapol. peak DSC)

In a particular embodiment of the invention, Form D is characterized by an XRPD diffraction pattern containing XRPD peaks at angles of diffraction 2Theta of approximately 6.1°, 16.8°, 22.6°.

In a particular embodiment of the invention, Form D is characterized by an XRPD diffraction pattern containing XRPD peaks at angles of diffraction 2Theta of approximately 6.1°, 11.0°, 16.8°, 22.6°.

In a particular embodiment of the invention, Form D is characterized by an XRPD diffraction pattern containing XRPD peaks at angles of diffraction 2Theta of approximately 6.1°, 8.1°, 11.0°, 13.5°, 15.4°, 16.8°, 18.4°, 19.2°, 19.5°, 21.1°, 21.4°, 22.6°, 24.7°, 28.1°.

Figure 4:
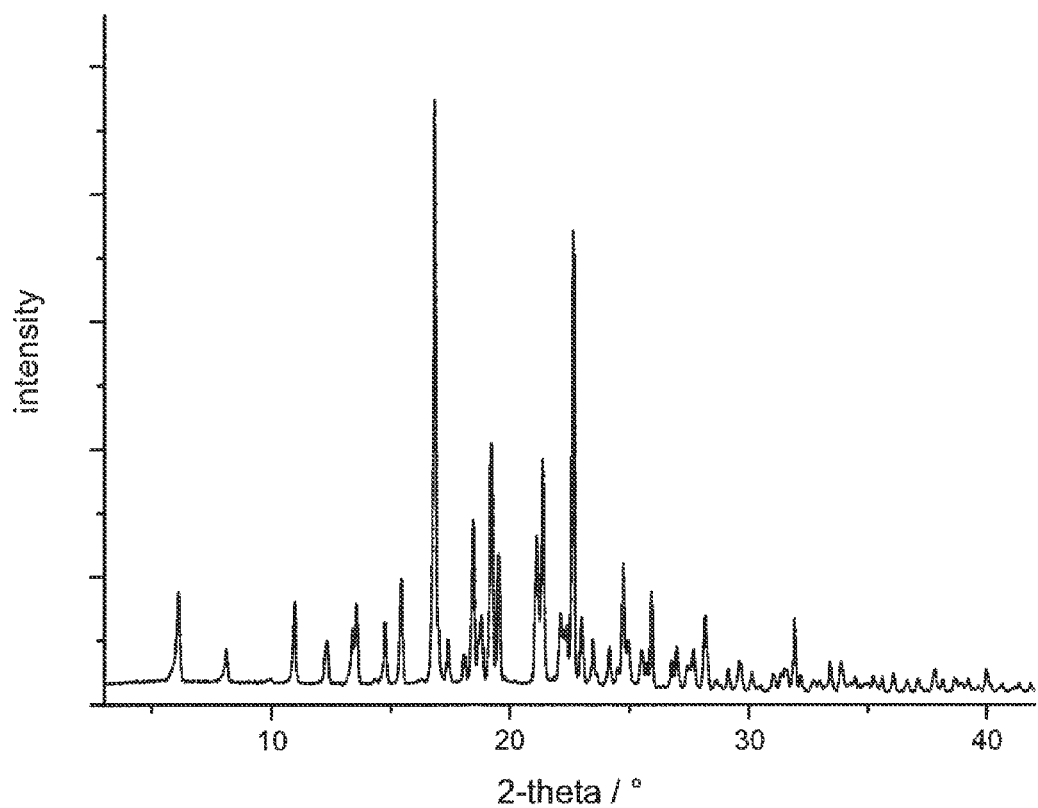
FIG. 4 depicts the XRPD pattern of Form D.

In a particular embodiment of the invention, Form D is characterized by the XRPD diffraction pattern of FIG. 4.

In a particular embodiment of the invention, Form D is characterized by an XRPD diffraction pattern containing XRPD peaks at peak positions as denoted in Table 5.

Figure 11:
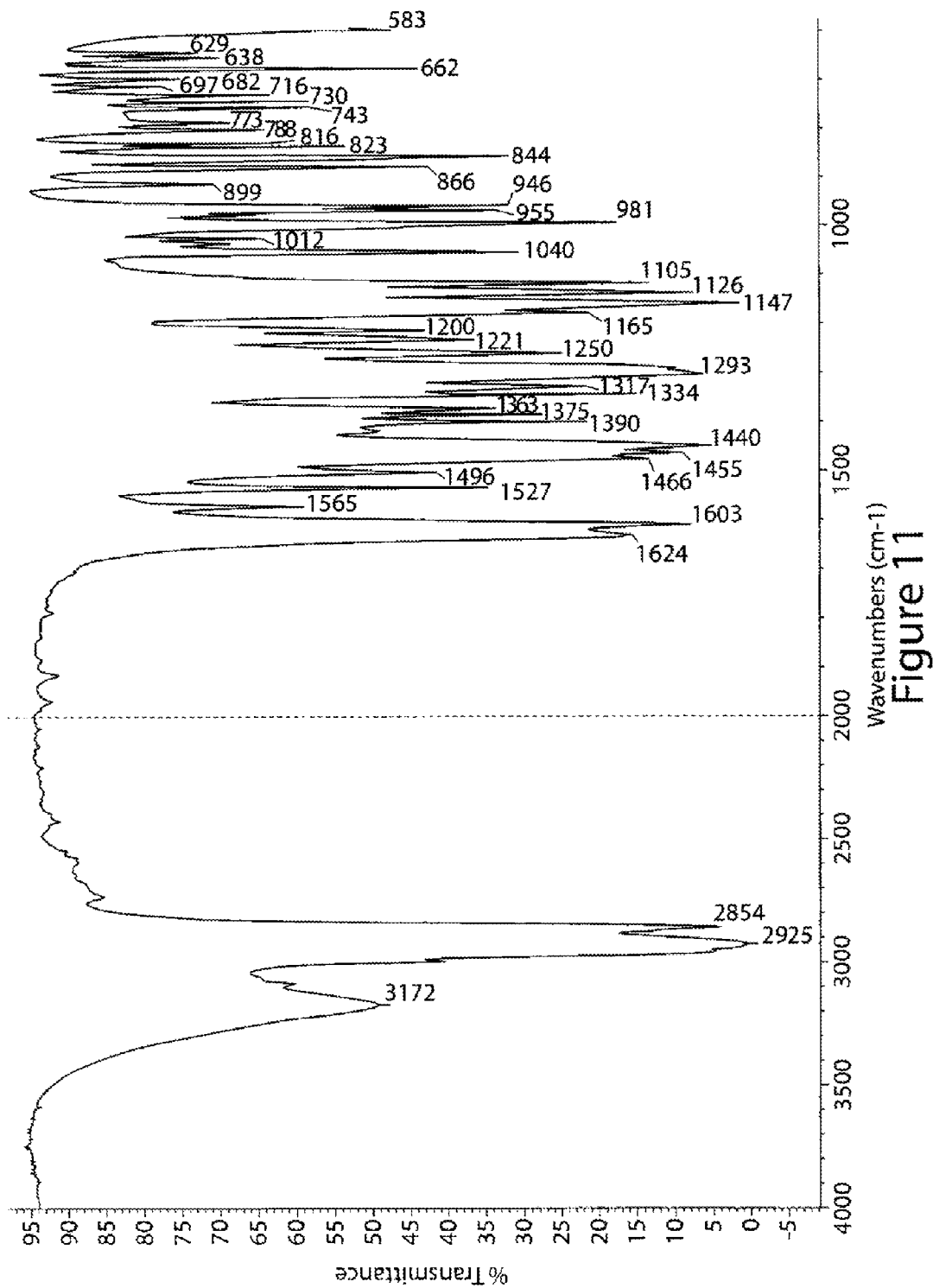
FIG. 11 depicts the FT-IR spectrum of Form D.

In a particular embodiment of the invention, Form D is characterized by the FTIR spectrum of FIG. 11.

In a particular embodiment of the invention, Form D is characterized by a melting point with onset temperature (DSC) in the range of about 96° C. to 100° C.

Form E of (1,1-dioxo-1λ$^6$-thiomorpholin-4-yl)-{6-[3-(4-fluoro-phenyl)-5-methyl-isoxazol-4-ylmethoxy]-pyridin-3-yl}-methanone is an anhydrate which exhibits only limited stability at ambient conditions. Form E is obtained by dehydration of Form B through storage at <5% rH. A rapid reconversion of Form E into Form B is observed upon exposure to >5% rH.

Similarly, also upon drying monohydrate form B by means of Humidity Controlled XRPD analysis Form E is observed at 0% rH.

One particular embodiment of the invention provides crystalline (1,1-dioxo-1λ$^6$-thiomorpholin-4-yl)-{6-[3-(4-fluoro-phenyl)-5-methyl-isoxazol-4-ylmethoxy]-pyridin-3-yl}-methanone in anhydrous polymorphic form E (Form E) as described herein.

In a particular embodiment of the invention, Form E is characterized by an XRPD diffraction pattern containing XRPD peaks at angles of diffraction 2Theta of approximately 16.5°, 20.8°.

In a particular embodiment of the invention, Form E is characterized by an XRPD diffraction pattern containing XRPD peaks at angles of diffraction 2Theta of approximately 13.1°, 16.5°, 20.8°.

In a particular embodiment of the invention, Form E is characterized by an XRPD diffraction pattern containing XRPD peaks at angles of diffraction 2Theta of approximately 5.5°, 13.1°, 13.3°, 14.2°, 16.5°, 19.1°, 20.8°, 22.3°, 23.9°, 25.1°, 25.5°, 26.4°, 29.0°.

In a particular embodiment of the invention, Form E is characterized by an XRPD diffraction pattern containing XRPD peaks at peak positions as denoted in Table 6.

Figure 5:
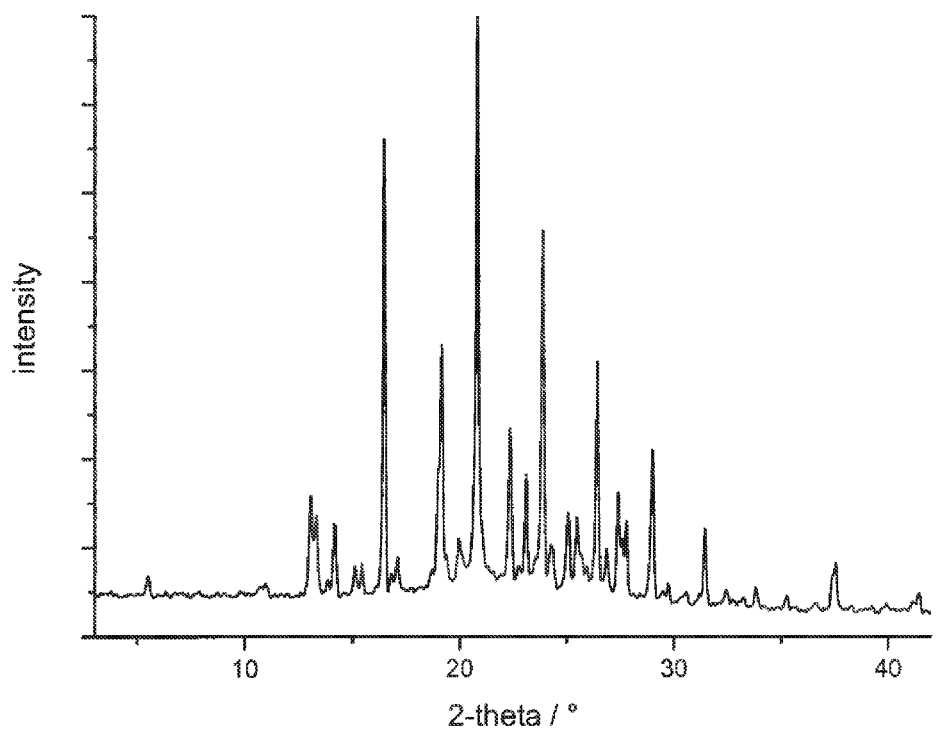
FIG. 5 depicts the XRPD pattern of Form E, analyzed at 0% rH or after drying at 70° C.

In a particular embodiment of the invention, Form E is characterized by the XRPD diffraction pattern of FIG. 5.

Figure 17:
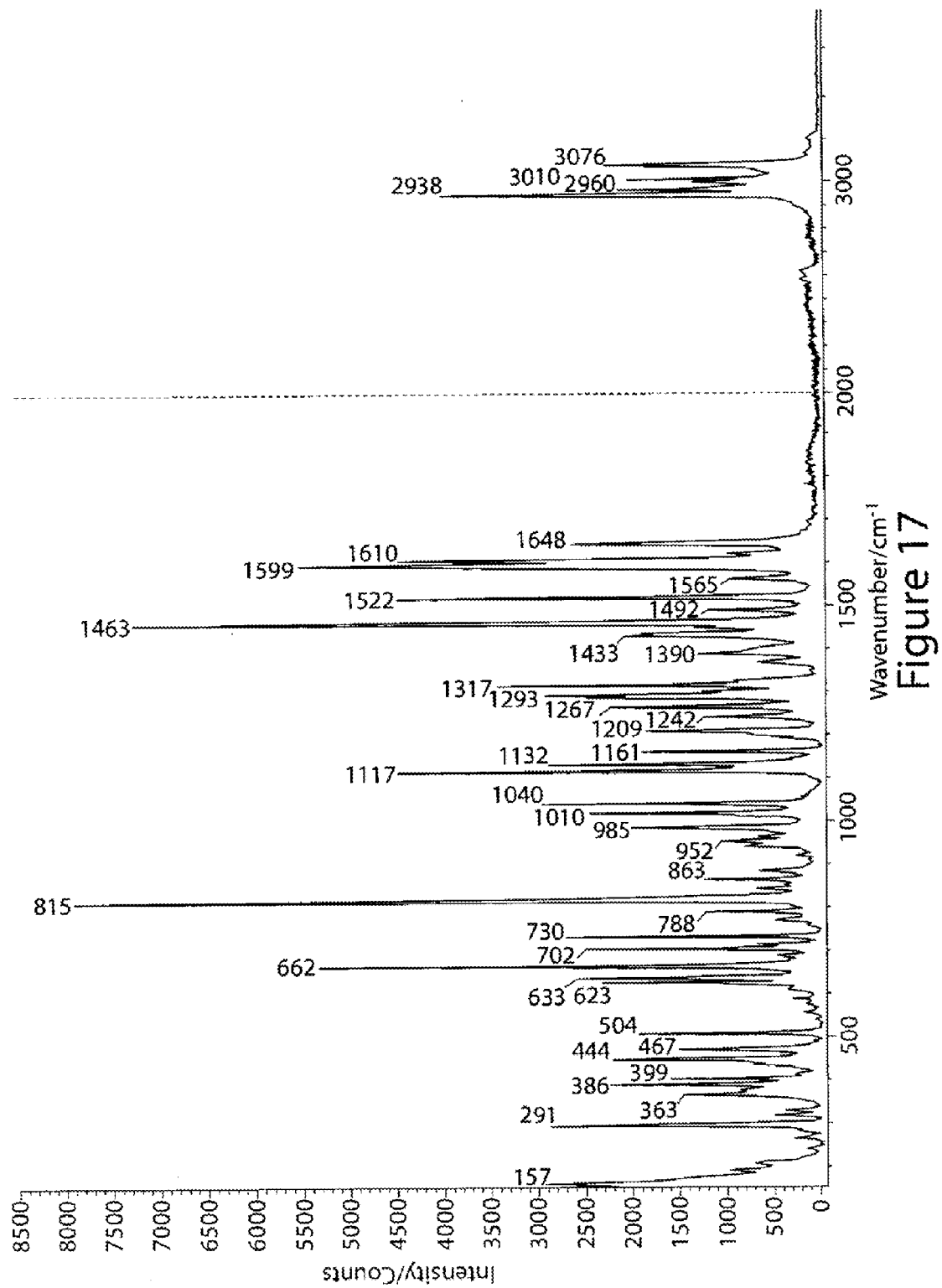
FIG. 17 depicts the Raman spectrum of Form E.

In a particular embodiment of the invention, Form E is characterized by the Raman spectrum of FIG. 17.

The glass transition temperature of the amorphous Form of (1,1-dioxo-1λ$^6$-thiomorpholin-4-yl)-{6-[3-(4-fluoro-phenyl)-5-methyl-isoxazol-4-ylmethoxy]-pyridin-3-yl}-methanone is approx. 66° C. (midpoint of second heating). Amorphous material is slightly hygroscopic, but no phase transformation has been observed upon storage at 100% rH at ambient temperature.

One particular embodiment of the invention provides amorphous (1,1-dioxo-1λ$^6$-thiomorpholin-4-yl)-{6-[3-(4-fluoro-phenyl)-5-methyl-isoxazol-4-ylmethoxy]-pyridin-3-yl}-methanone (Amorphous Form) as described herein.

In a particular embodiment of the invention, Amorphous Form is characterized by at least one amorphous halo and a lack of a sharp Bragg diffraction peak in the XRPD diffraction pattern.

Figure 6:
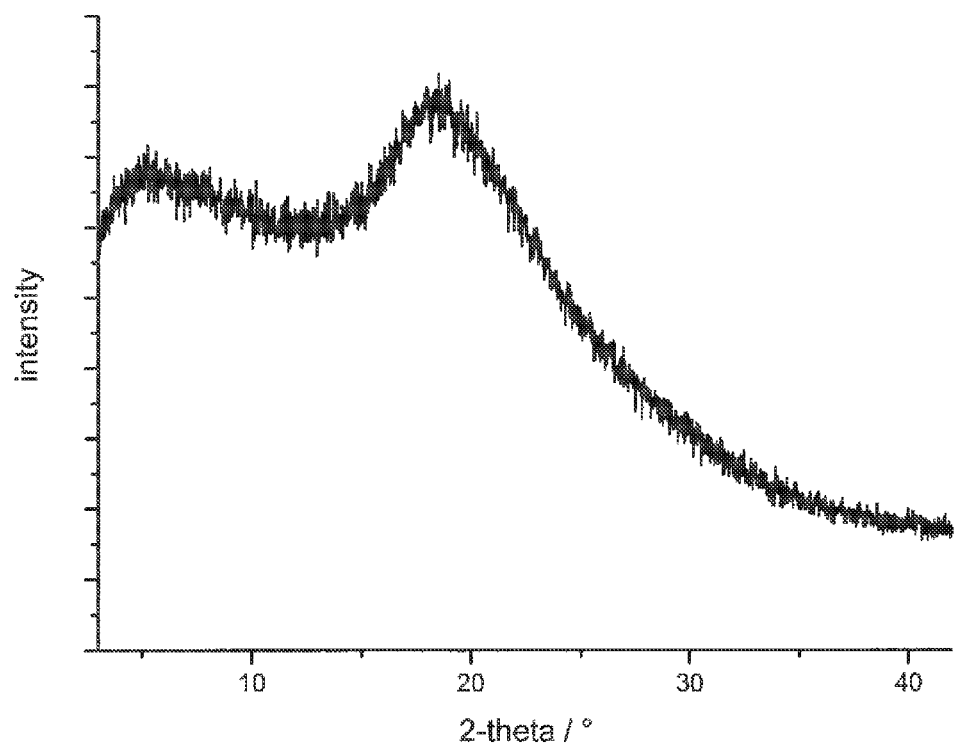
FIG. 6 depicts the XRPD pattern of amorphous Form.

In a particular embodiment of the invention, Amorphous Form is characterized by the XRPD diffraction pattern of FIG. 6.

Figure 12:
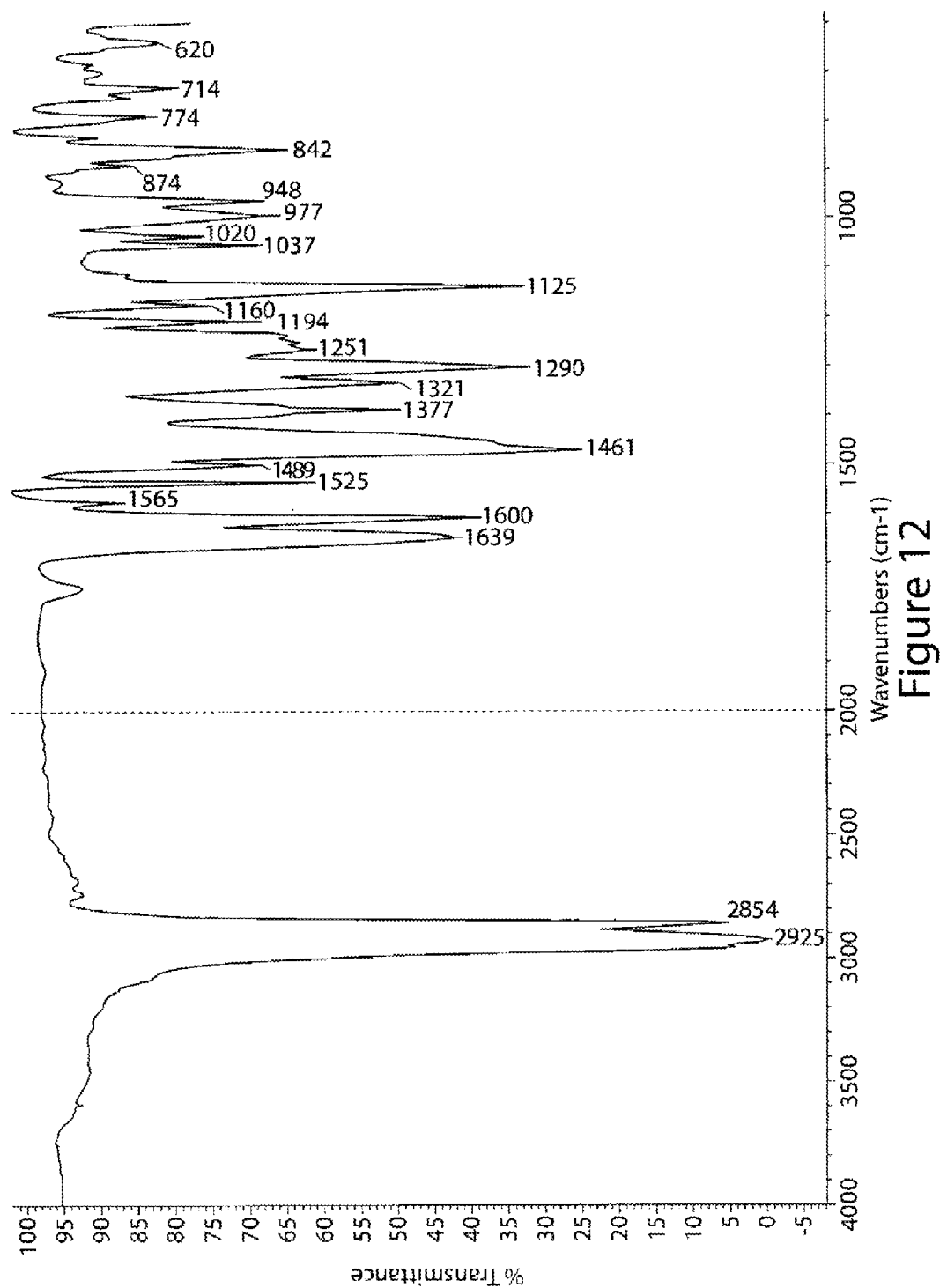
FIG. 12 depicts the FT-IR spectrum of amorphous Form.

In a particular embodiment of the invention, Amorphous Form is characterized by the FTIR spectrum of FIG. 12.

Figure 18:
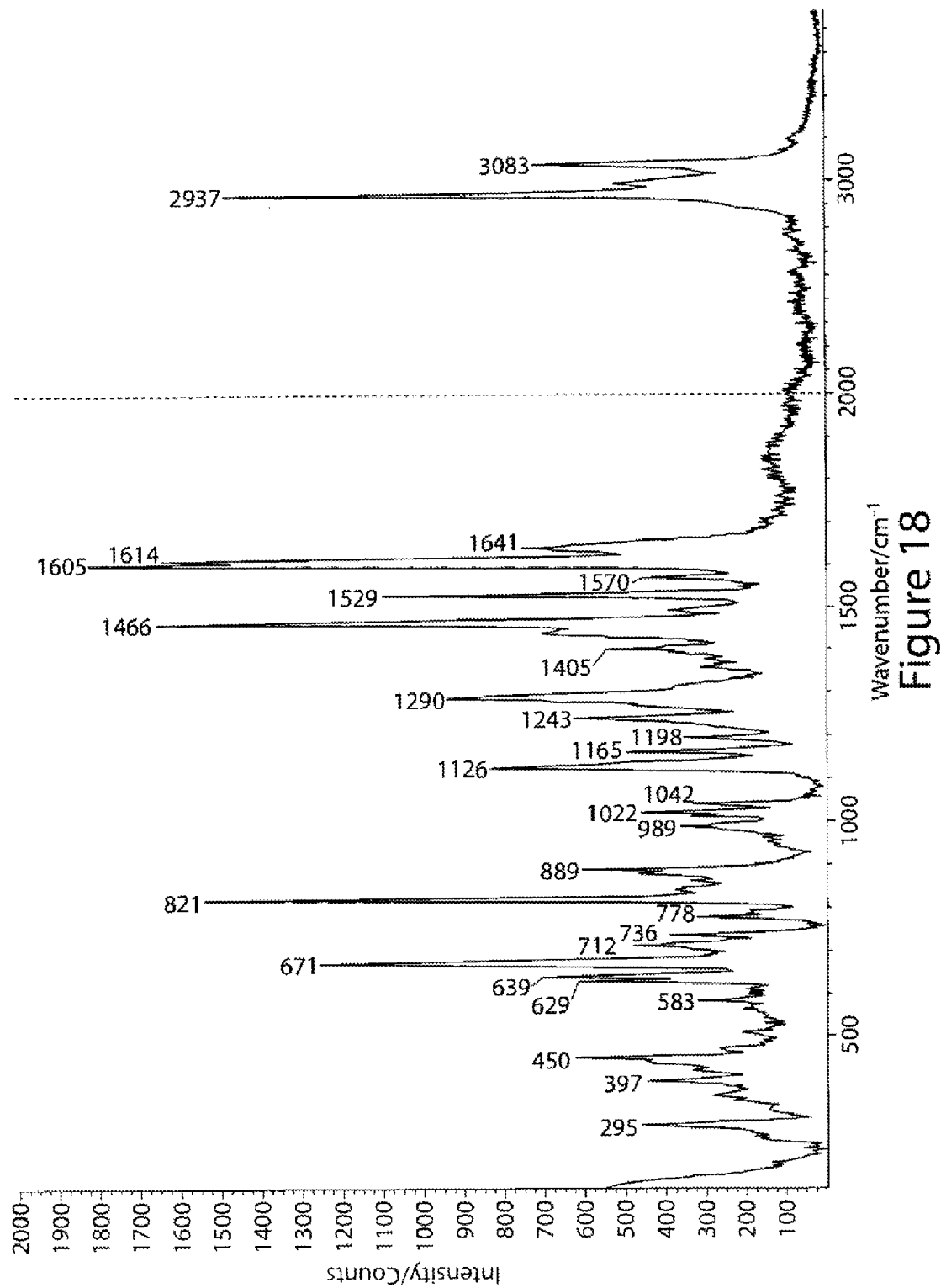
FIG. 18 depicts the Raman spectrum of amorphous Form.

In a particular embodiment of the invention, Amorphous Form characterized by the Raman spectrum of FIG. 18.

In a particular embodiment of the invention, Amorphous Form is characterized by a glass transition temperature Tg of 60° C. to 70° C., particularly 65° C. to 67° C., most particularly 66° C.

Figure 21:
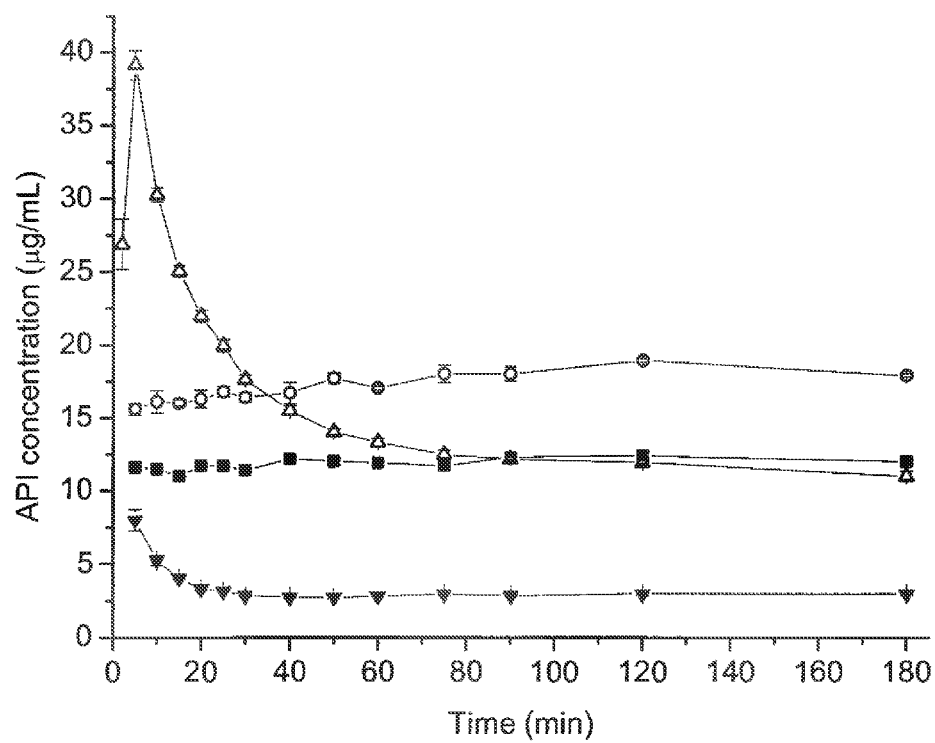
FIG. 21 illustrates the mean in vitro dissolution profiles in SGF. Mean in vitro dissolution profiles of micronized powders of Form A (○), Form B (▼), Form C (■) and γ-CD inclusion complex (Δ) in SGF at room temperature. Measurements were performed in triplicate (n=3).
Figure 22:
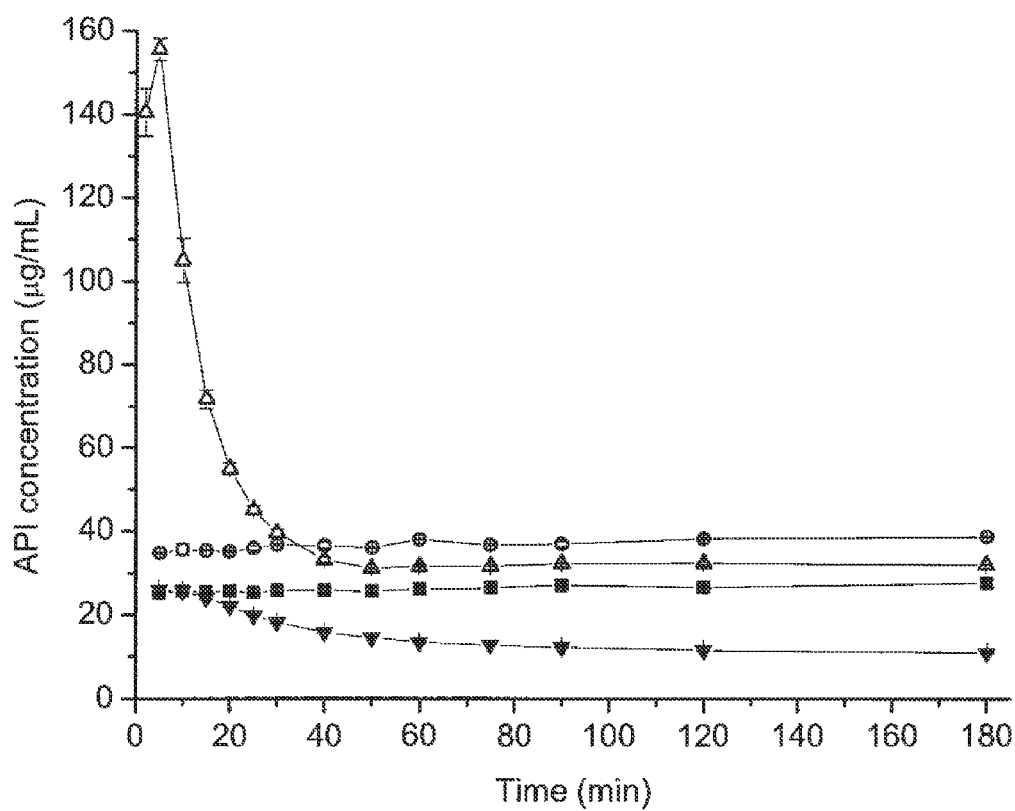
FIG. 22 illustrates the mean in vitro dissolution profiles in FeSSIF. Mean in vitro dissolution profiles of micronized powders of Form A (○), Form B (▼), Form C (■) and γ-CD inclusion complex (Δ) in FeSSIF at room temperature. Measurements were performed in triplicate (n=3).

In addition, the invention provides a 1:1 inclusion complex of (1,1-dioxo-1λ$^6$-thiomorpholin-4-yl)-{6-[3-(4-fluoro-phenyl)-5-methyl-isoxazol-4-ylmethoxy]-pyridin-3-yl}-methanone with γ-Cyclodextrin (γ-CD inclusion complex) with beneficial properties. The γ-CD inclusion complex is highly crystalline (as confirmed by XRPD). The dried γ-CD inclusion complex contains a residual water content of approximately 7.3% (as confirmed by TGA). Dried γ-CD inclusion complex and wet powder sample show different XRPD patterns. The crystal structure of the γ-CD complex seems to be dependent on the water content of the sample. Water seems to stabilize the crystal structure of the described inclusion complex and a substantial loss of water could lead to changes of the crystal structure. γ-CD inclusion complex containing residual water has an improved solubility in water as compared to dried γ-CD inclusion complexes [T. Toropainen et al., *Pharm. Res.* (2007) 24:1058-1066]. The molar ratio between API and γ-CD in the γ-CD inclusion complex is 1:1 (as confirmed by UPLC). A complex binding constant of 510.4 M$^{-1}$ was calculated for the inclusion complex of compounds of formula (I) and of γ-CD, as described herein. This binding constant and in vitro dissolution profiles indicate an increased dissolution rate and thus enhanced bioavailability as compared to other solid forms (FIGS. 21 & 22).

One particular embodiment of the invention provides a 1:1 inclusion complex of (1,1-dioxo-1λ$^6$-thiomorpholin-4-yl)-{6-[3-(4-fluoro-phenyl)-5-methyl-isoxazol-4-ylmethoxy]-pyridin-3-yl}-methanone with γ-Cyclodextrin (γ-CD inclusion complex) as described herein.

One particular embodiment of the invention provides a 1:1 inclusion complex of (1,1-dioxo-1λ$^6$-thiomorpholin-4-yl)-{6-[3-(4-fluoro-phenyl)-5-methyl-isoxazol-4-ylmethoxy]-pyridin-3-yl}-methanone with γ-Cyclodextrin (γ-CD inclusion complex) as described herein, containing a residual water content of 1% to 20% (w/w), particularly 5% to 15% (w/w), most particularly 8% to 12% (w/w).

In a particular embodiment of the invention, Form E is characterized by an XRPD diffraction pattern containing XRPD peaks at angles of diffraction 2Theta of approximately 7.4°, 14.9°, 16.7°, 21.8°.

In a particular embodiment of the invention, Form E is characterized by an XRPD diffraction pattern containing XRPD peaks at angles of diffraction 2Theta of approximately 7.4°, 12.1°, 14.9°, 16.7°, 21.8°.

In a particular embodiment of the invention, Form E is characterized by an XRPD diffraction pattern containing XRPD peaks at angles of diffraction 2Theta of approximately 3.8°, 5.2°, 7.4°, 9.2°, 10.6°, 11.5°, 11.8°, 12.1°, 14.2°, 14.9°, 15.8°, 16.7°, 19.2°, 20.3°, 21.2°, 21.8°, 22.5°, 23.7°, 26.8°.

Figure 7:
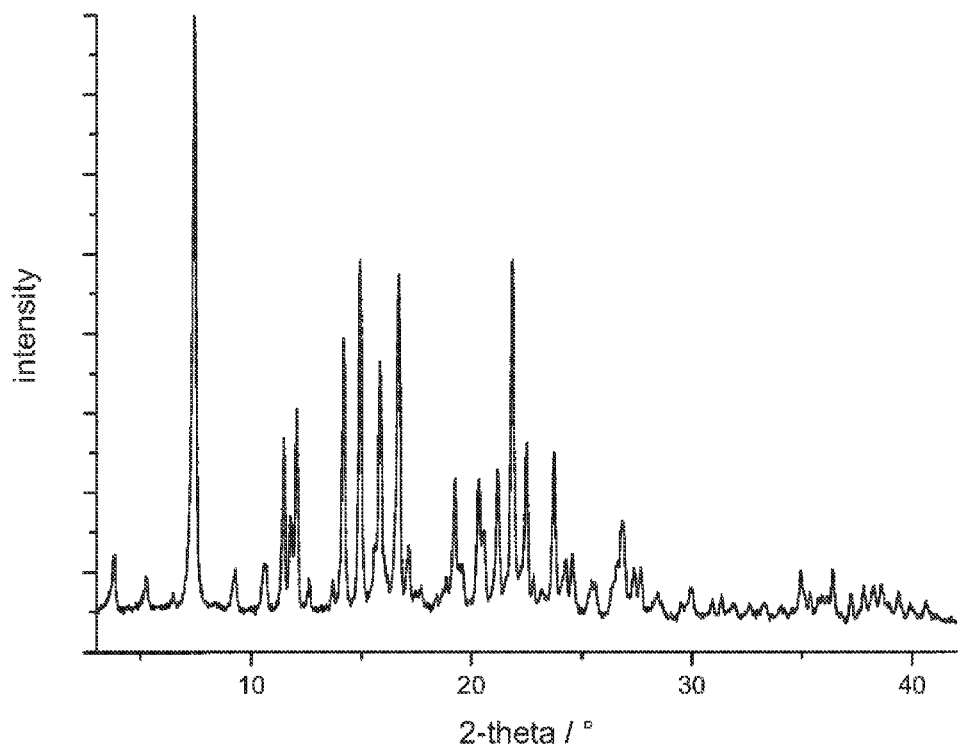
FIG. 7 depicts the XRPD pattern of γ-CD inclusion complex.

In a particular embodiment of the invention, γ-CD inclusion complex is characterized by the XRPD diffraction pattern of FIG. 7.

In a particular embodiment of the invention, γ-CD inclusion complex is characterized by an XRPD diffraction pattern containing XRPD peaks at peak positions as denoted in Table 7.

Figure 13:
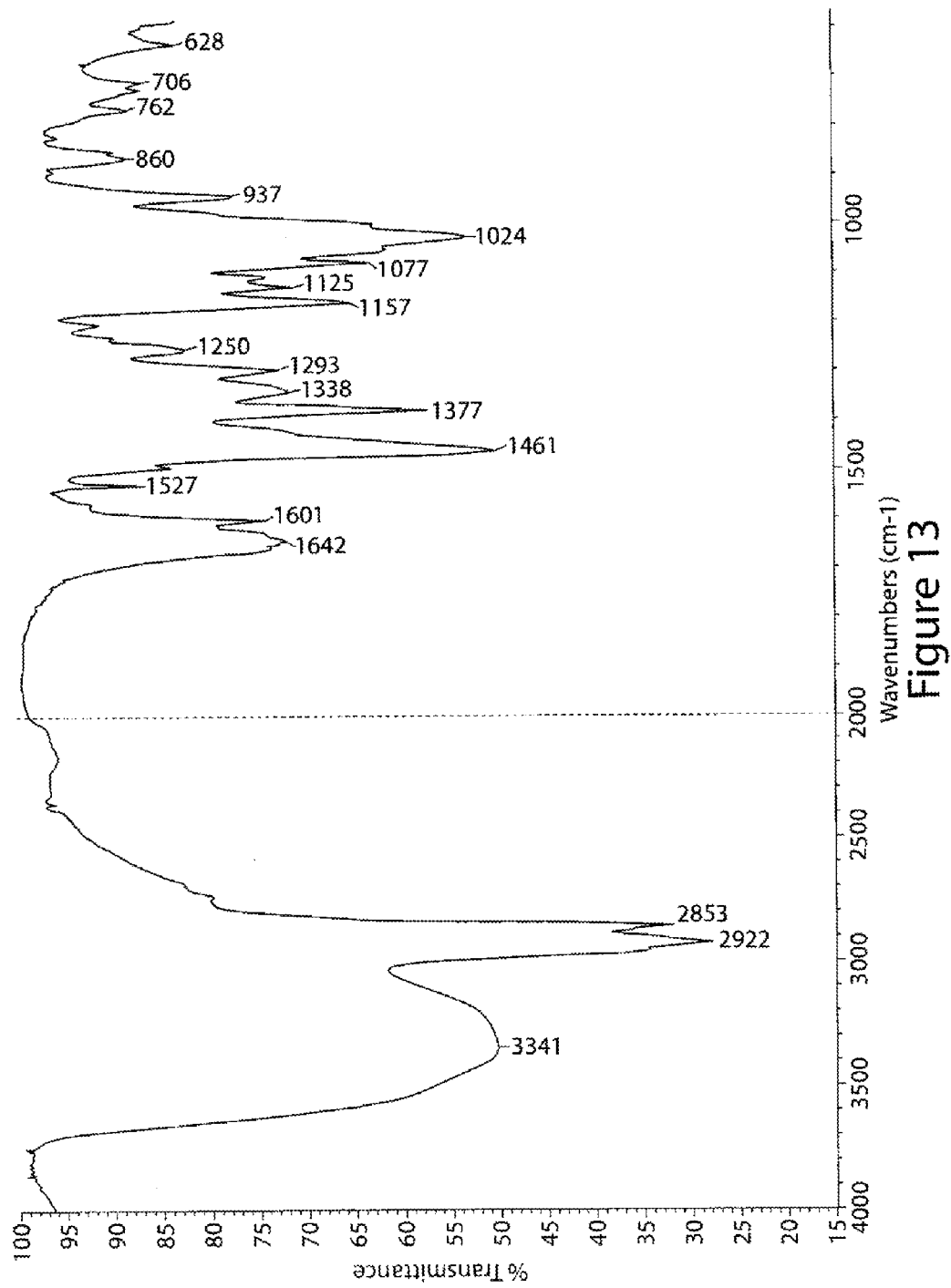
FIG. 13 depicts the FT-IR spectrum of γ-CD inclusion complex.

In a particular embodiment of the invention, γ-CD inclusion complex is characterized by the FTIR spectrum of FIG. 13.

Figure 19:
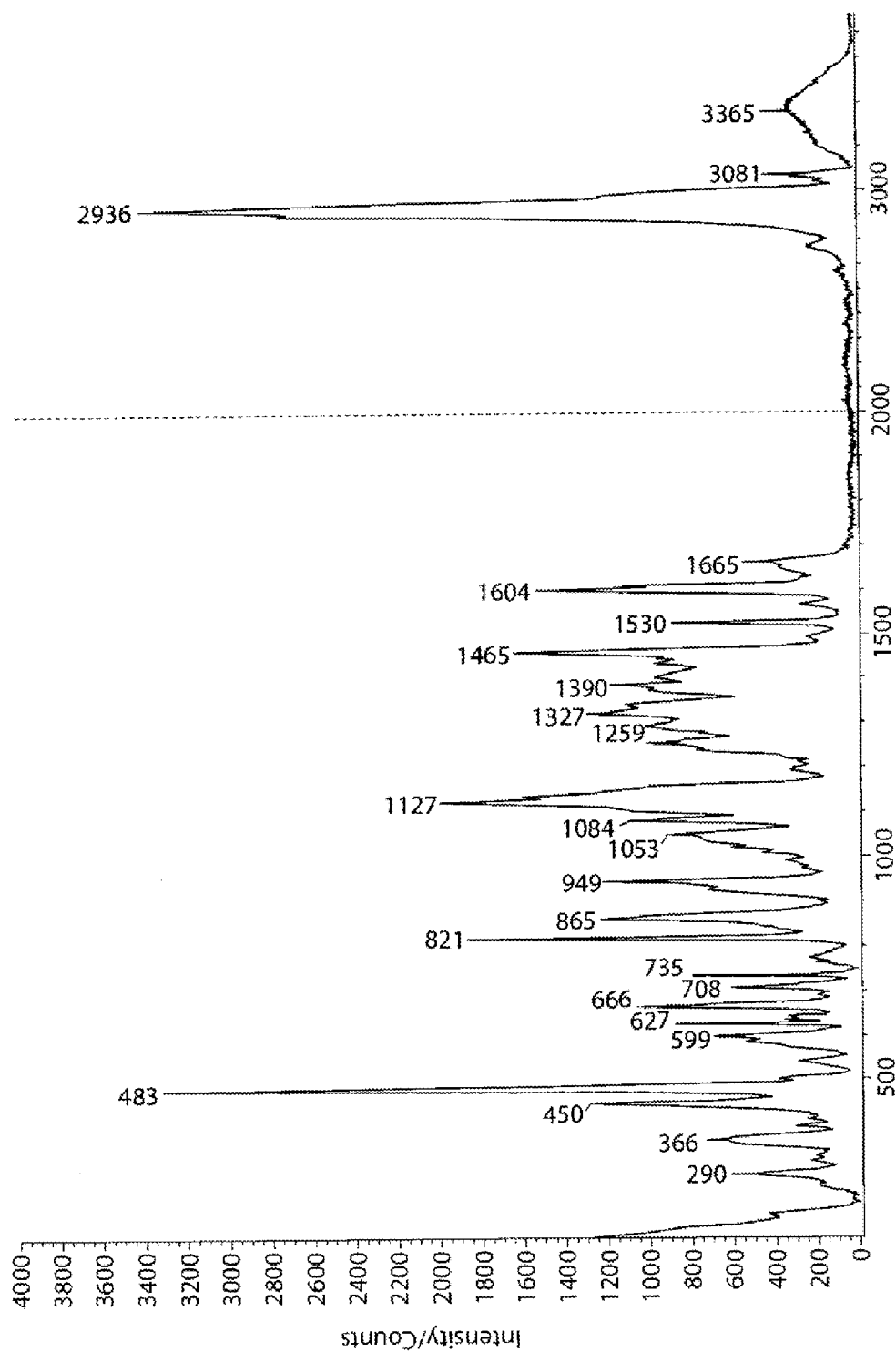
FIG. 19 depicts the Raman spectrum of γ-CD inclusion complex.

In a particular embodiment of the invention, γ-CD inclusion complex is characterized by the Raman spectrum of FIG. 19.

Table 1 lists the relevant crystal structure data of Form A, Form B, Form C and Form D of (1,1-dioxo-1λ$^6$-thiomorpholin-4-yl)-{6-[3-(4-fluoro-phenyl)-5-methyl-isoxazol-4-yl-methoxy]-pyridin-3-yl}-methanone. The crystal structures of Form A, Form B, Form C and Form D were refined. Form E crystallizes only at dry conditions and dehydrates at relative humidity>5%, single crystalline samples are not available.

The lattice constants, unit cell volume and calculated density are based on ambient temperature data. For this purpose the lattice constants obtained from single crystal structure analysis were refined with the experimental ambient conditions XRPD reference patterns using the software TOPAS 4.0, Bruker AXS.

TABLE 1

Single Crystal Structural Data of Forms A, B, C and D

| Crystal form | Form A | Form B | Form C | Form D |
|---|---|---|---|---|
| Solid form description | anhydrate | monohydrate | anhydrate | trifluoroethanol monosolvate |
| Measuring Temperature | 295K | 130K | 100K | 293K |
| Crystal system | Monoclinic | Monoclinic | Triclinic | Monoclinic |
| Space group | P2$_{(1)}$/c | P2$_{(1)}$/n | P1 | P2$_{(1)}$/c |
| Unit cell dimensions | | | | |
| a = | 26.1638 Å | 7.5969 Å | 7.653 Å | 14.6152 Å |
| b = | 6.3113 Å | 32.0909 Å | 7.8637 Å | 16.6069 Å |
| c = | 12.4695 Å | 8.9480 Å | 17.394 Å | 10.6567 Å |
| α = | 90° | 90° | 81.078° | 90° |
| β = | 90.836° | 110.454° | 78.195° | 98.934° |
| γ = | 90° | 90° | 87.98° | 90° |
| Cell volume | 2058.84 Å$^3$ | 2043.91 Å$^3$ | 1012.2 Å$^3$ | 2555.1 Å$^3$ |
| API molecules in unit cell | 4 | 4 | 2 | 4 |
| Calculated density | 1.437 g/cm$^3$ | 1.506 g/cm$^3$ | 1.462 g/cm$^3$ | 1.418 g/cm$^3$ |

*ambient temperature data

Tables 2, 3 and 4: XRPD peak positions and relative intensities of major XRPD peaks of Forms A, B and C.

TABLE 2

Form A

| 2Theta/° | rel. int./% * |
|---|---|
| 3.3 | 16.2 |
| 10.1 | 20.2 |
| 14.2 | 89.6 |
| 14.4 | 100 |
| 15.7 | 60.6 |
| 16.1 | 28.6 |
| 17.2 | 39.9 |
| 17.3 | 43.5 |
| 19.5 | 47.3 |
| 19.8 | 41.7 |
| 20.2 | 82.8 |
| 20.8 | 25.7 |
| 22.5 | 94.1 |
| 24.8 | 24 |
| 25.0 | 28.1 |
| 25.9 | 93.4 |
| 27.7 | 25.5 |

TABLE 3

Form B

| 2Theta/° | rel. int./% * |
|---|---|
| 10.9 | 28.8 |
| 13.0 | 28.7 |
| 13.3 | 70.4 |
| 14.1 | 27.3 |
| 14.8 | 49.9 |
| 16.5 | 45.7 |
| 17.0 | 29.9 |
| 18.9 | 49.6 |
| 20.6 | 98.6 |
| 21.0 | 52.8 |
| 22.5 | 100 |
| 23.4 | 43.1 |
| 24.8 | 32 |
| 26.9 | 33.1 |

TABLE 4

Form C

| 2Theta/° | rel. int./% * |
|---|---|
| 5.2 | 8.2 |
| 10.5 | 14.4 |
| 11.7 | 15.5 |
| 14.2 | 8.1 |
| 16.3 | 26.2 |
| 16.7 | 32.8 |
| 17.4 | 34.9 |
| 17.9 | 8.9 |
| 19.3 | 25.6 |
| 23.4 | 100 |
| 24.7 | 15.3 |
| 25.1 | 14.7 |
| 25.9 | 31.3 |

*Relative intensities may vary considerably from one measurement to another.

Tables 5, 6 and 7: XRPD peak positions and relative intensities of major XRPD peaks of Forms D, E and γ-CD inclusion complex.

TABLE 5

Form D

| 2Theta/° | rel. int./% * |
|---|---|
| 6.1 | 18.1 |
| 8.1 | 9.1 |
| 11.0 | 16.9 |
| 13.5 | 16.2 |
| 15.4 | 20.7 |
| 16.8 | 100 |
| 18.4 | 30.7 |
| 19.2 | 43.7 |
| 19.5 | 25.1 |
| 21.1 | 27.2 |
| 21.4 | 39.7 |
| 22.6 | 78.2 |
| 24.7 | 22.8 |
| 28.1 | 14.6 |

TABLE 6

Form E

| 2Theta/° | rel. int./% * |
|---|---|
| 5.5 | 9.7 |
| 13.1 | 23.4 |
| 13.3 | 19.2 |
| 14.2 | 18.7 |
| 16.5 | 81 |
| 19.1 | 47.7 |
| 20.8 | 100 |
| 22.3 | 34.4 |
| 23.9 | 66.8 |
| 25.1 | 20.4 |
| 25.5 | 19.8 |
| 26.4 | 45.1 |
| 29.0 | 31 |

TABLE 7

γ-CD inclusion complex

| 2Theta/° | rel. int./% * |
|---|---|
| 3.8 | 14.8 |
| 5.2 | 11.6 |
| 7.4 | 100 |
| 9.2 | 12.1 |
| 10.6 | 13.8 |
| 11.5 | 32.9 |
| 11.8 | 21.3 |
| 12.1 | 38.6 |
| 14.2 | 49.7 |
| 14.9 | 61.1 |
| 15.8 | 47.1 |
| 16.7 | 60 |
| 19.2 | 27.2 |
| 20.3 | 26.9 |
| 21.2 | 28.6 |
| 21.8 | 62.3 |
| 22.5 | 32.9 |
| 23.7 | 31.3 |
| 26.8 | 20.7 |

*Relative intensities may vary considerably from one measurement to another.

The invention further provides a distillative solvent exchange process for the preparation of solid forms of compounds of formula (I) as defined above comprising:

a) dissolution of the educt solid form in a solvent;

b) distillation of the solvent while keeping the reactor liquid level constant by replacing the distillate by an antisolvent;

c) physical separation of the desired solid form from the suspension.

In a particular embodiment, the desired solid form obtained by such distillative solvent exchange in step c) is crystalline (1,1-dioxo-1$\lambda^6$-thiomorpholin-4-yl)-{6-[3-(4-fluoro-phenyl)-5-methyl-isoxazol-4-ylmethoxy]-pyridin-3-yl}-methanone in anhydrous polymorphic form C (Form C) as defined above.

In a particular embodiment, the educt solid form in step a) is selected from Form A or Form B, most particularly from Form B.

In a particular embodiment, the solvent employed in step a) is selected from THF, DMF or acetone or a mixture thereof, particularly selected from THF.

In a particular embodiment, the antisolvent employed in step b) is selected from ethanol, iso-propanol, or n-heptane or a mixture thereof, particularly selected from ethanol.

In a particular embodiment, step b) is performed at increased temperature, particularly at 50-80° C.

In a particular embodiment, step b) is performed at reduced pressure, particularly at 100-300 mbar.

In a particular embodiment, step b) is optionally preceded or accompanied by seeding with the desired solid form as a powder or suspension, most particularly seeding with 1-10% (w/w) (in respect of final yield) of the desired solid form as a powder or suspension.

In a particular embodiment, the physical separation in step c) is performed via filtration.

The invention further provides a high-shear process for the preparation of solid forms of compounds of formula (I) as defined above comprising:

a) injection of a solution of the educt solid form in a solvent into a high-shear mixer comprising an antisolvent;

b) agitation of the rotor-stator system of the high-shear mixer;

c) physical separation of the desired solid form from the suspension.

In a particular embodiment, the desired solid form obtained by this high-shear process in step f) is crystalline (1,1-dioxo-1$\lambda^6$-thiomorpholin-4-yl)-{6-[3-(4-fluoro-phenyl)-5-methyl-isoxazol-4-ylmethoxy]-pyridin-3-yl}-methanone in anhydrous polymorphic form C (Form C) as defined above.

In a particular embodiment, the educt solid form in step d) is selected from Form A or Form B, particularly selected from Form B.

In a particular embodiment, the solution of educt solid form in step d) is injected at a constant flow rate of 1.6 g/min.

In a particular embodiment, the solvent employed in step d) is selected from THF, DMF or acetone or a mixture thereof, particularly selected from THF.

In a particular embodiment, the antisolvent employed in step d) is selected from ethanol, iso-propanol, or n-heptane or a mixture thereof, particularly selected from n-heptane.

In a particular embodiment, the antisolvent is circulated across the high-shear mixer in steps d) and e) at a constant velocity, particularly at a constant velocity of 20 l/h.

In a particular embodiment, the antisolvent of step d) optionally comprises seeding particles of the desired solid form, particularly 1-10% (w/w) (in respect of final yield) of seeding particles of the desired solid form, most particularly 5-10% (w/w) (in respect of final yield) of seeding particles of the desired solid form.

In a particular embodiment, the rotor-stator system in step e) is rotated at a rotation rate of 15000 RPM to 24000 RPM.

In a particular embodiment, steps d) and e) are performed at decreased temperature, particularly at −20° C. to 0° C., most particularly at −5° C.

In a particular embodiment, the physical separation in step f) is performed via filtration.

Another embodiment provides pharmaceutical compositions or medicaments comprising solid forms of compounds of formula (I) as described herein and a pharmaceutically acceptable excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The solid forms of compounds of formula (I) as described herein can be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The solid forms of compounds of formula (I) as described herein can be administered in any convenient administrative form, e.g., tablets, powders, capsules, solutions, dispersions, suspensions, syrups, sprays, suppositories, gels, emulsions, patches, etc. Such compositions can contain components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also contain still other therapeutically valuable substances.

A typical formulation is prepared by mixing a solid form of compounds of formula (I) as described herein and a pharmaceutically acceptable excipient. Suitable excipients are well known to those skilled in the art and are described in detail in, e.g., Ansel H. C. et al., *Ansel's Pharmaceutical Dosage Forms and Drug Delivery Systems* (2004) Lippincott, Williams & Wilkins, Philadelphia; Gennaro A. R. et al., *Remington: The Science and Practice of Pharmacy* (2000) Lippincott, Williams & Wilkins, Philadelphia; and Rowe R. C, *Handbook of Pharmaceutical Excipients* (2005) Pharmaceutical Press, Chicago. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which solid forms of compounds of formula (I) as described herein can be administered can vary within wide limits and will, of course, be fitted to the individual requirements in each particular case. In general, in the case of oral administration a daily dosage of about 0.1 to 1000 mg per person of a solid form of compounds of formula (I) as described herein should be appropriate, although the above upper limit can also be exceeded when necessary. A particular embodiment of the invention provides a daily dosage of 0.1 to 1000 mg (p.o.), particularly of 10 to 500 mg (p.o.), most particularly of 75 to 350 mg (p.o.).

An example of a suitable oral dosage form is a tablet containing about 100 mg to 500 mg of a solid form of compounds of formula (I) as described herein compounded with about 90 to 30 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving a solid form of compounds of formula (I) as described herein, for example 10 to 100 mg, in a suitable buffer solution, e.g. a phosphate buffer, adding a tonicifier, e.g. a salt such as sodium chloride, if desired. The solution can be filtered, e.g., using a 0.2 µm filter, to remove impurities and contaminants.

The solid forms of compounds of formula (I) as described herein, possess valuable pharmacological properties and are ligands for GABA A α5 receptors. The solid forms of compounds of formula (I) of the present invention can therefore be used, either alone or in combination with other drugs, for the treatment or prevention of diseases which are modulated by ligands for GABA A receptors containing the α5 subunit. These diseases include, but are not limited to, acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke, Multiple Sclerosis (MS), acute Meningitis, Fetal Alcohol Syndrome, attentional disorders, CNS conditions occurring after stroke, and need for cognition enhancement.

The invention therefore also provides pharmaceutical compositions containing solid forms of compounds of formula (I) as described herein and a pharmaceutically acceptable excipient.

The invention likewise provides solid forms of compounds of formula (I) as described herein for use as therapeutically active substances.

The invention likewise provides solid forms of compounds of formula (I) as described herein for use as therapeutically active substances for the treatment or prevention of diseases which are related to the GABA A α5 receptor.

The invention likewise provides solid forms of compounds of formula (I) as described herein for use as therapeutically active substances for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke, Multiple Sclerosis (MS), acute Meningitis, Fetal Alcohol Syndrome, and attentional disorders, for stroke recovery therapy, or for use as cognitive enhancers.

In another embodiment, the invention provides a method for the treatment or prevention of diseases which are related to the GABA A α5 receptor, which method comprises administering solid forms of compounds of formula (I) as described herein to a human being or animal.

In another embodiment, the invention provides a method for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke, Multiple Sclerosis (MS), acute Meningitis, Fetal Alcohol Syndrome, and attentional disorders, for stroke recovery therapy, or for cognition enhancement, which method comprises administering solid forms of compounds of formula (I), particularly compounds of formula (I), as described herein to a human being or animal.

The invention also provides the use of solid forms of compounds of formula (I) as described herein for the treatment or prevention of diseases which are related to the GABA A α5 receptor.

The invention also provides the use of solid forms of compounds of formula (I) as described herein for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke, Multiple Sclerosis (MS), acute Meningitis, Fetal Alcohol Syndrome, and attentional disorders or for cognition enhancement.

The invention also provides the use of solid forms of compounds of formula (I) as described herein for the preparation of medicaments for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke, Multiple Sclerosis (MS), acute Meningitis, Fetal Alcohol Syndrome, and attentional disorders, for stroke recovery therapy, or for the preparation of cognitive enhancers. Such medicaments contain a compound as described above.

More particularly, the present invention provides the use of solid forms of compounds of formula (I) as described herein for the treatment, prevention and/or delay of progression of CNS conditions caused by neurodevelopmental defects which result in excessive GABAergic inhibition in the cortex and hippocampus, wherein the CNS condition is selected from cognitive deficits in Down Syndrome, in autism, in neurofibromatosis type I, or after stroke.

The treatment or prevention of cognitive disorders, Alzheimer's disease, schizophrenia, positive, negative and/or cognitive symptoms associated with schizophrenia, Down syndrome, and neurofibromatosis type I, are particular embodiments of present invention.

A particular embodiment of the invention provides the treatment or prevention of Alzheimer's disease.

A particular embodiment of the invention provides the treatment or prevention of Down syndrome.

A particular embodiment of the invention provides the treatment or prevention of neurofibromatosis type I.

A particular embodiment of the invention provides the recovery after stroke.

EXAMPLES

The following examples 1-28 are provided for illustration of the invention. They should not be considered as limiting the scope of the invention, but merely as being representative thereof.

Example 1

Preparation of crystalline (1,1-dioxo-1$\lambda^6$-thiomorpholin-4-yl)-{6-[3-(4-fluoro-phenyl)-5-methyl-isoxazol-4-ylmethoxy]-pyridin-3-yl}-methanone in anhydrous polymorphic form A Form A Form A can be prepared as described in WO 2009/071476.

Step a: (E)- and/or (Z)-4-Fluoro-benzaldehyde oxime

To a suspension of 4-fluorobenzaldehyde (24.8 g, 200 mmol) (6.75 g, 54 mmol) and hydroxylamine hydrochloride (4.16 g, 60 mmol) in ethanol (4.3 mL) and water (13 mL) was added ice (25 g). Then a solution of sodium hydroxide (5.5 g, 138 mmol) in water (6.5 mL) was added dropwise within a 10 min period (temperature rises from −8° C. to +7° C.) whereupon most of the solid dissolves. After 30 min stirring at room temperature a white solid precipitated and the resulting mixture was then diluted with water and acidified with HCl (4 N). The white precipitate was then filtered off, washed with water and dried under high vacuum to afford the title compound (23.3 g, 84%) which was obtained as a white solid. MS: m/e=139.1 [M]+.

Step b: (E)- and/or (Z)—N-Hydroxy-4-fluoro-benzenecarboximidoyl chloride

To a solution of (E)- and/or (Z)-4-fluoro-benzaldehyde oxime (23.3 g, 167 mmol) (6.9 g, 50 mmol) in DMF (50 mL) was added N-chlorosuccinimide (6.6 g, 50 mmol) portionwise over 1 h, keeping the temperature below 35° C. The reaction mixture was stirred at room temperature for 1 h. The mixture was then poured onto ice-water, and extracted with ethyl acetate. The combined organic layers were then washed with water and brine, dried over sodium sulfate and evaporated to afford the title compound (25.9 g, 89%) which was obtained as an off white solid. MS: m/e=173.0 [M]+.

Step c: 3-(4-Fluoro-phenyl)-5-methyl-isoxazole-4-carboxylic acid ethyl ester

To a solution of (E)- and/or (Z)—N-hydroxy-4-fluoro-benzenecarboximidoyl chloride (15.4 g, 89 mmol) (11.1 g, 64 mmol) in diethylether (151 mL) was added ethyl 2-butynoate (7.2 g, 7.5 mL, 64 mmol) at 0° C. followed by the dropwise addition of triethylamine (7.8 g, 10.7 mL, 77 mmol) and the resulting mixture allowed to warm up to room temperature overnight. The mixture was then poured onto ice-water, and extracted with diethylether. The combined organic layers were then washed with water and brine, dried over sodium sulfate and evaporated. Purification by chromatography (SiO2, heptane:ethyl acetate=100:0 to 1:1) afforded the title compound (9.8 g, 44%) which was obtained as an off white solid. MS: m/e=250.1 [M+H]+.

Step d: [3-(4-Fluoro-phenyl)-5-methyl-isoxazol-4-yl]-methanol

To a solution of 3-(4-fluoro-phenyl)-5-methyl-isoxazole-4-carboxylic acid ethyl ester (3.0 g, 12 mmol) (6.18 g, 25 mmol) in THF (320 mL) was added portionwise lithiumaluminiumhydride (528 mg, 14 mmol) at 0° C. and the reaction mixture was stirred at room temperature for 3 h. The mixture was then cooled to 0° C. and water (518 µL) added followed by sodium hydroxide (15% solution, 518 µL) and then again water (1.5 mL) and the mixture then stirred overnight at room temperature. The precipitate was then filtered off and washed with THF. The combined washings and filtrate were then evaporated. Purification by chromatography (SiO2, heptane: ethyl acetate=100:0 to 1:1) afforded the title compound (1.8 g, 71%) which was obtained as a white solid. MS: m/e=208.1 [M+H]+.

Step e: 6-[3-(4-Fluoro-phenyl)-5-methyl-isoxazol-4-ylmethoxy]-nicotinic acid methyl ester To a suspension of sodium hydride (55% dispersion in mineral oil, 852 mg, 20 mmol) in THF (27 mL) was added a solution of [3-(4-fluoro-phenyl)-5-methyl-isoxazol-4-yl]-methanol (103 mg, 0.55 mmol) (3.68 g, 18 mmol) in THF (54 mL) at 0° C. and the reaction mixture warmed to room temperature over 30 min. Then a solution of methyl 6-chloronicotinate (3.35 g, 20 mmol) in THF (1.5 mL) was added dropwise at 0° C. and the reaction mixture was stirred at room temperature overnight. The reaction mixture was then poured into aqueous sodium chloride (saturated) and the mixture was extracted with ethyl acetate. The combined organic layers were then washed with water and brine and then dried over sodium sulfate, filtered and evaporated. Purification by chromatography (SiO2, heptane:ethyl acetate=7:3) afforded the title compound (81 mg, 47%) which was obtained as a light yellow solid. MS: m/e=343.3 [M+H]+.

Step f: 6-[3-(4-Fluoro-phenyl)-5-methyl-isoxazol-4-ylmethoxy]-nicotinic acid

To a solution of 6-[3-(4-fluoro-phenyl)-5-methyl-isoxazol-4-ylmethoxy]-nicotinic acid methyl ester (1.4 g, 4.2 mmol) (538 mg, 1.1 mmol) in THF (5 mL) was added a solution of lithium hydroxide monohydrate (94 mg, 2.2 mmol) in water (5 mL) and methanol (1 mL) added and the resulting mixture stirred at room temperature overnight. The mixture was acidified to pH 4 with HCl (25%, 3 drops) and methanol (2 drops) added. A gum began to form and the mixture was cooled at 0° C. for 1.5 h and then the aqueous layer decanted off. Trituration with diethylether and hexane afforded the title compound (1.1 g, 78%) which was obtained as a white solid. MS: m/e=327.3 [M−H]−.

Step g: crystalline (1,1-dioxo-1$\lambda^6$-thiomorpholin-4-yl)-{6-[3-(4-fluoro-phenyl)-5-methyl-isoxazol-4-ylmethoxy]-pyridin-3-yl}-methanone in anhydrous polymorphic form A (Form A)

To a solution of 6-[3-(4-fluoro-phenyl)-5-methyl-isoxazol-4-ylmethoxy]-nicotinic acid (99 mg, 0.33 mmol (69 mg, 0.2 mmol)) in DMF (300 µL) were added 2-(1H-benzotriazole-1-yl)-1,1,3,3-tetramethyluronium tetrafluoroborate (71 mg, 0.22 mmol), N,N-diisopropyl ethyl amine (171 µL, 1.0 mmol) and thiomorpholine-S,S-dioxide (17.3 µL, 0.22 mmol). The resulting reaction mixture was stirred for 1 h at room temperature. Concentration and purification by chromatography (SiO2, heptane:ethyl acetate=100:0 to 1:1) afforded the title compound (73 mg, 55%) as a white solid. MS: m/e=446.1 [M+H]+.

Example 2

Preparation of Form A

A solution of 0.1 g of (1,1-dioxo-1$\lambda^6$-thiomorpholin-4-yl)-{6-[3-(4-fluoro-phenyl)-5-methyl-isoxazol-4-ylmethoxy]-pyridin-3-yl}-methanone in 0.7 mL of 2-pentanol or THF was crash-cooled with liquid nitrogen, isolated by centrifugation at 25° C. and dried at 20° C. and reduced pressure at <5 mbar for 2 d.

Example 3

Preparation of Form A 152.4 mg of 1,1-dioxo-1$\lambda^6$-thiomorpholin-4-yl)-{6-[3-(4-fluoro-phenyl)-5-methyl-isoxazol-4-ylmethoxy]-pyridin-3-yl}-methanone were dissolved in 2.14 mL of 2-pentanol at 60° C. yielding a colorless solution. The solvent was evaporated slowly until dryness (perforated cover foil, 5 d at ambient conditions) to yield blade-like crystals.

Example 4

Preparation of Form A 700.0 g of 6-[3-(4-fluoro-phenyl)-5-methyl-isoxazol-4-ylmethoxy]-nicotinic acid (Ex. 1 step f), 10 L of THF and 469.0 g of 1,1-carbodiimidazol were stirred at ambient temperature for one hour. 407.0 g of thiomorpholine-S,S-dioxide, 12.0 g of 4-dimethylaminopyridine and 340 mL of triethylamine p.a. were added successively and refluxed under stirring over two nights. Additional 82.0 g of thiomorpholine-S,S-dioxide and 68.0 mL of triethylamine p.a. were added and further refluxed under stirring overnight (o.n.). The experiment was cooled down to approx. 30° C. 10 L of desalinated water and 16 L of ethanol were added successively. The emerging solution was cooled down to 20° C., seeded with 12 g of Form A and stirred at ambient temperature for 30 min. The suspension was reduced to 16 L at max. 35° C. In order to replace THF, 20 L of ethanol were added. The suspension was stirred at ambient temperature o.n. and then filtrated. The filter cake was rinsed with 7.4 L of a 1:1 desalinated water/ethanol mixture and dried at 50° C. o.n. yielding 820 g of Form A (86%).

Example 5

Preparation of Form A 16.32 g of Form B were dissolved in 257 g THF at 50° C. To remove the water from the solution 172 g of THF were distilled off under reduced pressure at 80° C. Then this water free product solution was cooled to room temperature.

Keeping the jacket temperature constant at −5° C., 238 g of heptane were circulated across a high-shear-mixer device with a velocity of 20l/h by use of a peristaltic pump. After 5 Minutes the high-shear-mixer was started with a rotation rate of 15000 RPM to 24000 RPM and the product solution from above was pumped with a flow rate of 1.6 g/min directly through the injector into the rotor-stator system. After addition was completed, the resulting crystals were filtered and dried at 40° C. at 30 mbar for 15 h to yield Form A.

Example 6

Preparation of Form A 100 g of Form B were dissolved in 1200 g THF at 50° C. About 50% of THF were distilled off at 70° C. under reduced pressure (800 mbar) to yield a 20% (w/w) solution of Form B in THF. In a distillative solvent exchange, THF/water (of hydration) was exchanged against dry THF at 800 mbar and at 70° C. while keeping the solvent level constant until the water content was below 0.1% (w/w). 888 g of heptane at 5° C. as antisolvent were seeded with 1% (w/w) of Form A. Subsequently the product solution was cooled to 50° C. and was dosed during 30 minutes using a temperate hose underneath surface to the heptane present at 5° C. The resulting crystals were filtered and dried at reduced pressure until constant weight to yield Form A (92%).

Example 7

Preparation of Form A 41 g of Form B were dissolved in 170 g THF at 50° C. 30 g of ethanol were added and the solution cooled to 30° C. In a distillative solvent exchange, the solvent (THF/ethanol) was exchanged to the anti-solvent ethanol at a temperature of 30° C. and at reduced pressure (300 mbar) while the volume was kept constant by continuously replacing the distillate by a total of 340 g of ethanol. 20 minutes after start of the distillation, crystallization was initiated by seeding with 2% (w/w) of crystals of Form A. Subsequently the pressure was reduced to 230 mbar. 50 minutes after start of the distillation, the pressure was reduced to 130 mbar. 67 minutes after start of the distillation, the solvent exchange was completed. The resulting suspension was stirred for 1.5 h at ambient temperature and subsequently filtered. The obtained crystals were dried in a vacuum dryer at 40° C. over-night to yield 36.4 g of Form A (92.4%).

Example 8

Preparation of crystalline (1,1-dioxo-1$\lambda^6$-thiomorpholin-4-yl)-{6-[3-(4-fluoro-phenyl)-5-methyl-isoxazol-4-ylmethoxy]-pyridin-3-yl}-methanone monohydrate in polymorphic form B (Form B)

Step a) (E)- and/or (Z)-4-fluoro-benzaldehyde oxime

To a suspension of 4-fluoro-benzaldehyde (30.4 g, 0.24 mol) in water (50 mL) was added at 0-5° C. within 5 minutes a solution of hydroxylamine hydrochloride (17.7 g, 0.25 mol) in water (30 mL) and the resulting mixture stirred for 15 minutes at 0-5° C. The mixture was then treated at 15-25° C. within 15 minutes with 32% NaOH (24.44 mL, 0.26 mol) and the resulting suspension was stirred for one additional hour and then extracted with ethyl acetate (3×100 mL). The combined organic layers were washed with water (2×100 mL) and subsequently concentrated to dryness to afford 31.9 g (95%) of the title oxime as a white solid.

Step b) 3-(4-Fluoro-phenyl)-5-methyl-isoxazole-4-carboxylic acid ethyl ester

To a suspension of 4-fluoro-benzaldehyde oxime (1.39 g, 10.0 mmol) in DMF (10 mL) was added portionwise within 5 minutes at 15 to 20° C. N-chlorosuccinimide (1.36 g, 10.0 mmol) and the resulting mixture was stirred at room temperature for 90 minutes. The yellow solution (containing N-Hydroxy-4-fluoro-benzenecarboximidoyl chloride) was then treated within 2 minutes at room temperature with a solution of ethyl-3-(1-pyrrolidino)crotonate (1.89 g, 10.0 mmol) in 5 mL of DMF and the resulting solution was stirred at room temperature for 28 hours. The mixture was diluted with water (25 mL) and subsequently extracted with ethyl acetate (4×25 mL). The combined organic layers were washed with 1 M HCl (2×25 mL) and water (2×25 mL), dried over Na2SO4 and subsequently concentrated to dryness (45° C./25 mbar) to afford 2.37 g (95%) of the title ester as a brownish solid with a purity of 100% (by GC) and 97% (by HPLC).

Step c) 3-(4-Fluoro-phenyl)-5-methyl-isoxazole-4-carboxylic acid

A mixture of 179.5 g (0.72 mol) of 3-(4-Fluoro-phenyl)-5-methyl-isoxazole-4-carboxylic acid ethyl ester in 880 g of ethanol 95% was stirred at 20-30° C. for 40 minutes and then treated with 78.5 g of solid sodium hydroxide. The resulting mixture was stirred for 5 h at 20-30° C. Ethanol was removed in vacuum at 45-50° C. and the residue was subsequently treated with 500 g of water at 20-30° C. to afford a clear solution. The solution was stirred for 40 minutes and filtered. To the filtrate was added 235 g of methyl tert-butyl ether and 600 g of water and the resulting mixture stirred for 20 min and then stood for 20 min. The layers were separated and the aqueous layer was acidified to pH<1 with hydrochloric acid. The crystals were filtered and washed with water to provide 147 g crude wet product. The crude wet product was suspended in 680 g of toluene and the mixture was heated at 75-85° C. for 7 h. The mixture was cooled to 20-30° C. and stirred for 1 hour at this temperature. The crystals were filtered off and dried at 50-55° C. in vacuum over night to afford 137 g (86% yield) of the title acid as a white to slightly yellow solid with a purity of 99.9% (HPLC).

Step d) [3-(4-Fluorophenyl)-5-methyl-isoxazol-4-yl]-methanol

A suspension of 448 g of tetrahydrofuran and 95 g (0.70 mol) of zinc chloride was stirred at 20-30° C. for 1 h. 23.6 g (0.62 mol) of sodium borohydride were added in portions at 20-38° C. and the mixture subsequently stirred at 60-65° C. for 3 h. A solution of 69 g (0.31 mol) of 3-(4-Fluoro-phenyl)-5-methyl-isoxazole-4-carboxylic acid in 220 g THF was added dropwise and the resulting mixture stirred at 60-65° C. for 16 h. The reaction was then quenched by the drop wise addition of mixture of 93 g of HCl in 202 g of water at 5-10° C. The mixture was stirred at this temperature for 2 h to dissolve the solids completely. The solvent was removed under reduced pressure with a jacket temperature of 35-40° C. To the residue were added 510 g of water. The resulting suspension was cooled to 20-30° C. and the crystals were filtered off and washed with water. The crude wet product was stirred for 1 h in a mixture of 150 g of water, 31 g of HCl and 419 g of MTBE. The lower aqueous phase was removed and organic phase was dried with 25 kg of anhydrous sodium sulfate, stirred for 0.5 h and filtered under nitrogen. The filtrate was almost completely concentrated under reduced pressure at 40-45° C. The residue was treated at 20-25° C. with 100 g of MTBE. The mixture was stirred at 55-60° C. for 2 h, cooled to 0° C. and subsequently stirred at this temperature for additional 2 h. The crystals were filtered off and dried at 45-50° C. in vacuum over night to afford 42 g (66% yield) of the title alcohol as an off-white solid with a purity of 99.9% (HPLC).

Step e) 6-[3-(4-Fluoro-phenyl)-5-methyl-isoxazol-4-ylmethoxy]-nicotinonitrile

To a suspension of sodium hydride (60% in mineral oil, 7.9 g, 181 mmol, 1.5 eq.) in THF (65 mL) was added within 30 minutes at room temperature a solution of [3-(4-Fluorophenyl)-5-methyl-isoxazol-4-yl]-methanol (25.0 g, 121 mmol) and 6-chloronicotinonitrile (16.7 g, 121 mmol) in THF (120 mL) and the resulting mixture was stirred for one hour. A solution of citric acid (18.5 g, 96.5 mmol) in water (185 mL) was added to the reaction mixture within 30 minutes. From the resulting THF/water mixture THF was distilled off under reduced pressure at a jacket temperature of 60° C. and replaced by ethanol. In total 284 g of ethanol were added. The resulting suspension was stirred for one hour at room temperature. The crystals were filtered off, washed with a mixture of ethanol (60 mL) and water (60 mL) and subsequently dried at 50° C./<25 mbar to afford 36.5 g (91% corrected yield) of the title nitrile as an off-white solid with an assay of 93% (w/w).

Step f) 6-[3-(4-Fluoro-phenyl)-5-methyl-isoxazol-4-ylmethoxy]-nicotinic acid

6-[3-(4-Fluoro-phenyl)-5-methyl-isoxazol-4-ylmethoxy]-nicotinonitrile (58.8 g, 190 mmol) was suspended in water (440 mL) and ethanol (600 mL) and treated with 32% sodium hydroxide solution (178 mL 1.92 mol). The mixture was heated to 50-55° C. and subsequently stirred at this temperature for 15 hour. The slightly turbid mixture was polish filtered to remove the ether by-product 6-[3-(4-Fluoro-phenyl)-5-methyl-isoxazol-4-ylmethoxymethyl-3-(4-fluoro-phenyl)-5-methyl-isoxazole. The first vessel and the transfer lines were rinsed with a mixture of water (50 mL) and ethanol (50 mL). The filtrate was treated at 20-25° C. within one hour with 25% hydrochloric acid (approx. 280 mL) until the pH was <2.0. The resulting suspension was stirred for one hour at room temperature. The crystals were filtered off, washed with a mixture of ethanol (200 mL) and water (200 mL) and subsequently dried at 50° C./<25 mbar until constant weight to afford 52.0 g (83%) of the title acid as an off-white solid with a purity of 99.5%.

Step g) Purification of thiomorpholine-1,1-dioxide HCl

A mixture of 60 g of thiomorpholine-1,1-dioxide HCl in 600 mL THF, 105 mL water and 30 mL DMF was heated to 63-66° C. (slightly reflux) and the resulting clear to slightly turbid solution stirred at this temperature for 5 to 10 hours. The mixture was then treated at 63-66° C. within 30 minutes with 300 mL of THF. The mixture was then cooled to 0-5° C. within 3 hours and the resulting suspension stirred at this temperature for one additional hour. The crystals were filtered off, washed with THF (2×25 mL) and dried at 50° C. and under reduced pressure (<20 mbar) to afford 56.6 g (94%) of thiomorpholine-1,1-dioxide HCl with a purity of 100% (area) and a THF content of 0.14%.

Step h) crystalline (1,1-dioxo-1$\lambda^6$-thiomorpholin-4-yl)-{6-[3-(4-fluoro-phenyl)-5-methyl-isoxazol-4-ylmethoxy]-pyridin-3-yl}-methanone monohydrate in polymorphic form B (Form B)

6-[3-(4-Fluoro-phenyl)-5-methyl-isoxazol-4-ylmethoxy]-nicotinic acid (23.0 g, 70.1 mmol) and 1,1-carbonyldiimidazole (15.3 g, 94.6 mol, 1.35 eq.) were dissolved in THF (120 mL) and the resulting solution was stirred for one hour at room temperature. This solution was then added to a suspension of thiomorpholine-1,1-dioxide HCl (16.9 g, 98.5 mmol), DMAP (400 mg, 3.27 mmol) and triethylamine (9.78 g, 96.7 mmol) in THF (120 mL). The resulting mixture was heated to reflux temperature and subsequently stirred at this temperature for 50 hours. The mixture was cooled to room temperature and then treated within one hour with water (300 mL). From the resulting suspension THF was distilled off under reduced pressure and with a jacket temperature of 60° C. and continuously replaced by ethanol (426 g) at constant volume. The suspension was cooled to room temperature and stirred for 2 hours. The crystals were filtered off, washed with a mixture of ethanol (100 mL) and water (100 mL) and subsequently dried at 55° C./<25 mbar until constant weight to afford 28.9 g (92%) of Form B as a colorless solid with purity of 99.7% (area) as measured by HPLC.

Example 9

Preparation of Form B

Form A was aged for 8 days in an aqueous suspension. Isolation by filtration yielded crystalline blades which were rinsed with water and then dried at ambient conditions.

Example 10

Preparation of Form B 155.9 mg of Form A were dissolved in 2.2 mL of 15% water in acetone at 60° C. yielding a colorless solution. The solvent was evaporated slowly until dryness (perforated cover foil, 5 d at ambient conditions) to yield equant crystals.

Example 11

Preparation of Form B 509 mg of Form A were dissolved in 7.1 mL 15%-vol. water/acetone at 60° C. yielding a colorless solution. Then the solvent was allowed to evaporate slowly over 8 days (perforated cover foil, ambient conditions). The residue was dried at 20° C./<5 mbar o.n. (vacuum tray dryer), yielding 440 mg (86%) of equant crystals.

Example 12

Preparation of Form B 10.0 g of Form C were dissolved in 50 mL of THF and 17 mL of DMF under stirring at ambient temperature. During a period of 30 minutes, the solution was gradually heated to 50-55° C. and stirred at this temperature for 15 minutes. 75 mL of water were added dropwise during 2-3 hours under stirring at 50-55° C. The resulting suspension was stirred for additional 15 minutes at 50-55° C. and afterwards gradually cooled to 15-20° C. during 2-4 hours. The suspension was stirred for 5 hours at 15-20° C., filtered and washed with a small amount of water. The obtained crystals were dried for 12 hours at 40° C. at reduced pressure (20 mbar) yielding Form B (95%).

Example 13

Preparation of crystalline (1,1-dioxo-1λ$^6$-thiomorpholin-4-yl)-{6-[3-(4-fluoro-phenyl)-5-methyl-isoxazol-4-ylmethoxy]-pyridin-3-yl}-methanone in anhydrous polymorphic form C

Form C 4.5 kg of Form A were dissolved in 40 L of THF at ambient temperature. After polishing filtration the filter was rinsed by 5 L of THF. From the combined solutions solvent was distilled off at reduced pressure at a temperature below 70° C. while the volume was kept constant by continuously replacing the distillate by a total of 90 L of ethanol. The suspension was allowed to cool to ambient temperature over 12 hours. 25 L of ethanol were added, the suspension was heated to 78° C. at ambient pressure, allowed to cool to ambient temperature over 12 hours and stirred for one additional hour. Crystallization at ambient pressure occurred at 78° C. to 70° C. 25 L of ethanol were distilled off at reduced pressure at 35-40° C. and the suspension was allowed to cool to ambient temperature over 12 hours. The product was isolated by filtration and rinsed by 20 L of ethanol. The crystals were dried in a vacuum tray dryer (50° C./5 mbar for 3 d), yielding 4.1 kg (91%) colorless plate-like crystals. It was possible to reproduce the experiment on 10 g scale.

Example 14

Preparation of Form C 200 mg of Form A were stirred in 0.8 mL of ethyl acetate at ambient temperature for 14 days (suspension). After isolation of the solids by filtration and drying in a vacuum tray dryer (50° C./<5 mbar for 12 h) Form C was obtained. Alternatively, ethanol or toluene can be used instead of ethyl acetate.

Example 15

Preparation of Form C 41 g of Form B were dissolved in 170 g THF at 50° C. 30 g of ethanol were added and the solution cooled to 30° C. In a distillative solvent exchange, the solvent (THF/ethanol) was exchanged to the anti-solvent ethanol at a temperature of 30° C. and at reduced pressure (300 mbar) while the volume was kept constant by continuously replacing the distillate by a total of 340 g of ethanol. 20 minutes after start of the distillation, the pressure was reduced to 230 mbar. 30 minutes after start of the distillation, the previously clear yellow solution became opaque. Two minutes later the opaque solution had turned into a thick suspension. 50 minutes after start of the distillation, the pressure was reduced to 130 mbar. 68 minutes after start of the distillation, the solvent exchange was completed. The resulting suspension was stirred for 2 h at ambient temperature and subsequently filtered. The obtained crystals were dried in a vacuum dryer at 40° C. over-night to yield 35.8 g of Form C.

Example 16

Preparation of Form C 10 g of Form B (22.4 mmol) were dissolved in 350 mL THF under stirring at ambient temperature, filtered and the filter rinsed with 40 mL of THF. In a distillative solvent exchange, the solvent of the filtrate was exchanged to ethanol at a temperature of 60° C. and at reduced pressure (100-300 mbar) while the volume was kept constant by continuously replacing the distillate by a total of 200 mL of ethanol. Crystallization was initiated after addition of the first 20 ml of ethanol by seeding with crystals of Form C. The resulting suspension was stirred for 1 h at ambient temperature, subsequently filtered and rinsed with 50 mL of ethanol. The obtained crystals were dried in a vacuum dryer at 50° C. over-night to yield 8.8 g (88%) of Form C.

Example 17

Preparation of Form C 82 g (177 mmol) of Form B were dissolved in 340 g of THF at 50° C. 60 g of ethanol were added to prepare a 17% (w/w) solution of Form B in a THF/ethanol mixture of (85:15 (w/w). The clear solution was allowed to cool to 35° C. under stirring. A 10% (w/w) seeding suspension of 0.8 g of Form C suspended in 7.2 g of a 50:50 (w/w) THF/ethanol mixture (10% (w/w) Form C in respect of final theoretical yield) was added and the reaction mixture was stirred for 30 min at ambient temperature. The pressure was decreased to 300 mbar while the temperature was increased to 50° C. In a distillative solvent exchange, the volume was kept constant by continuously replacing the distillate by a total 680 g of ethanol, which were added linearly (5.6 g/min) during a total time of 120 minutes. The reaction pressure is lowered, after 20 minutes of ethanol addition to 230 mbar, and after 50 minutes of total ethanol addition to 130 mbar. After 115 minutes of ethanol addition, the temperature was gradually lowered to 5° C. during at a cooling speed of 1° C./min (30 min cooling time). The suspension was stirred for 30 minutes at 5° C., filtered and rinsed with 68 g of ethanol. The obtained crystals were dried at 40° C. at 30 mbar for 16 h to yield 98.5% of Form C.

Alternatively, this preparation can be performed with acetone as solvent instead of THF. Alternatively, this preparation can be performed with isopropanol and/or n-heptane as anti-solvent instead of ethanol.

Example 18

Preparation of Form C 16.32 g of Form B were dissolved in 257 g THF at 50° C. To remove the water from the solution 172 g of THF were distilled off under reduced pressure at 80° C. Then this water free product solution was cooled to room temperature.

To 238 g Heptane at a temperature of −5° C. 1.6 g (10% (w/w) in respect of final theoretical yield) of Form C were added under stirring as seeding material. Keeping the jacket temperature constant at −5° C., the resulting suspension was circulated across a high-shear-mixer device with a velocity of 20 l/h by use of a peristaltic pump. After 5 minutes the high-shear-mixer was started with a rotation rate of 15000 RPM to 24000 RPM and the product solution from above was pumped with a flow rate of 1.6 g/min. directly through the injector into the rotor-stator system. After addition was completed, the resulting crystals were filtered and dried at 40° C. at 30 mbar for 15 h to yield 91% of Form C with an average particle size d50<10 µm.

When conducting Example 18 without seeds, Form A was obtained (see Example 5). Using 2% (w/w) Form C seeds, a mixture from Form A (dominant) and C was obtained. Employing 5% (w/w) Form C seeds, a mixture from Form C (dominant) and A was obtained.

Example 19

Preparation of Form C 14.12 g of Form B were dissolved in 240 g THF at 50° C. To remove the water from the solution 160 g of THF were distilled off under reduced pressure at 80° C. The water free solution was cooled during 15 minutes to 25° C. and 0.07 g Form C seeds (0.5% (w/w) in respect of final theoretical yield) were added. After 30 minutes of stirring the temperature was lowered over 135 minutes to 15° C. and 9.0 g heptane were added in parallel. The resulting suspension was stirred for 30 minutes, then the temperature was raised over 15 minutes to 35° C. After 30 minutes the temperature is cooled again over 165 minutes to 15° C. and another 11 g of heptane were added in parallel. After 30 minutes of stirring the temperature was raised again to 35° C. and the suspension was stirred again for 30 minutes. Afterwards the temperature was lowered again to 15° C. during 495 minutes and 33 g heptane were added in parallel. The resulting final suspension was stirred for additional 120 minutes, then filtered, dried at 40° C. and 30 mbar for 16 hours to yield 94% of Form C with an average particle size d50>50 µm.

Example 20

Preparation of crystalline (1,1-dioxo-1$\lambda^6$-thiomorpholin-4-yl)-{6-[3-(4-fluoro-phenyl)-5-methyl-isoxazol-4-ylmethoxy]-pyridin-3-yl}-methanone trifluoroethanol mono-solvate in polymorphic form D (Form D)

40 mg of Form A was equilibrated in 400 µl 3:1 trifluoroethanol/methanol (TFE/MeOH) mixture for 7 days at room temperature by head-over-head rotation with magnetic stir bars in 2 mL HPLC glass crimp vials. After equilibration the solid phase was separated from the liquid phase by centrifugation. The solvent was removed by a pipette and by strips of filter paper. The residual solids were dried at 40° C. in a vacuum tray dryer to 10 h at 20 mbar.

Example 21

Preparation of Form D 2 g of Form A were dissolved in 20 mL of a 3:1 trifluoroethanol/methanol mixture. Seed crystals of Form D were added and the mixture was stored closed at ambient temperature for 3 days. The residual column-shaped crystals were isolated by filtration (glass filter) and dried in a vacuum tray dryer (ambient temperature/20 mbar for 24 h).

Example 22

Preparation of crystalline (1,1-dioxo-1$\lambda^6$-thiomorpholin-4-yl)-{6-[3-(4-fluoro-phenyl)-5-methyl-isoxazol-4-ylmethoxy]-pyridin-3-yl}-methanone in anhydrous polymorphic form E Form E 50 mg of Form B was subjected to dehydration/hydration cycles. At <5% rH reversible transformation into Form E was observed by means of Humidity Controlled XRPD.

Example 23

Preparation of Form E 50 mg of Form B was placed into a desiccator, where the sample was dried over concentrated sulfuric acid for 36 h at ambient temperature.

Example 24

Preparation of amorphous (1,1-dioxo-1$\lambda^6$-thiomorpholin-4-yl)-{6-[3-(4-fluoro-phenyl)-5-methyl-isoxazol-4-ylmethoxy]-pyridin-3-yl}-methanone (Amorphous Form)

0.554 g of Form C was dissolved in 4.0 mL of dichloromethane in a round bottom flask. The clear solution was rapidly concentrated using a rotary evaporator (40° C. outside temperature, vacuum stepwise reduced to 14 mbar). The residue was dried in a vacuum tray dryer (50° C./<5 mbar for 2 days), yielding 0.498 g (90%) of a colorless powder.

Example 25

Preparation of Amorphous Form 150 mg of Form A were molten at 160° C. in a glass vial using a heat gun and cooled to ambient temperature to yield amorphous material.

Example 26

Preparation of 1:1 inclusion complex of (1,1-dioxo-1$\lambda^6$-thiomorpholin-4-yl)-{6-[3-(4-fluoro-phenyl)-5-methyl-isoxazol-4-ylmethoxy]-pyridin-3-yl}-methanone with γ-Cyclodextrin (γ-CD inclusion complex)

300 mg of Form A was weighed into a 20 mL screw cap glass vial. 6 mL deionized water and γ-CD at a molar ratio of 1:2 was added. The suspension was equilibrated at room temperature for 32 days by head-over-head rotation using a Heidolph Reax 2 mixer (VWR International AG, Dietikon, Switzerland). Solid liquid separation was performed with amicon Ultrafree-MC® centrifugal filter devices (0.45 μm Durapore PVDF membrane, Millipore, Bedford, Mass.) to yield crystals of the γ-CD inclusion complex.

Example 27

Phase Solubility Analysis

Figure 20:
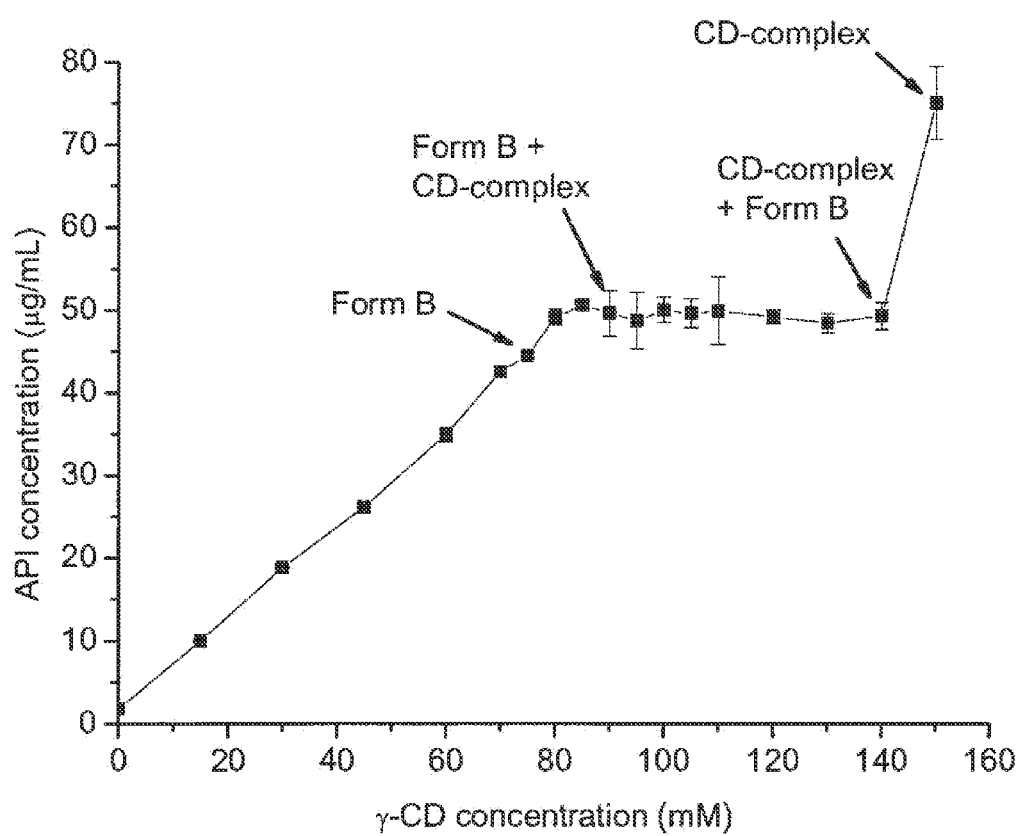
FIG. 20 illustrates the phase solubility diagram of (1,1-dioxo-1$\lambda^6$-thiomorpholin-4-yl)-{6-[3-(4-fluoro-phenyl)-5-methyl-isoxazol-4-ylmethoxy]-pyridin-3-yl}-methanone and γ-CD. The API solubility is shown in [μg/mL]. The solid phase in equilibrium with the saturated solution was verified at selected points (arrows) by Raman and XRPD measurements to identify and confirm potential solid-state transformations, such as formation of polymorph B (monohydrate) from the initially used polymorph A, or conversion of the free API to the γ-CD inclusion complex.

Phase solubility diagrams are used to characterize complex formation between two compounds and represent the solubility of the API as a function of the cyclodextrin concentration. The phase solubility diagram of (1,1-dioxo-1$\lambda^6$-thiomorpholin-4-yl)-{6-[3-(4-fluoro-phenyl)-5-methyl-isoxazol-4-yl-methoxy]-pyridin-3-yl}-methanone with γ-cyclodextrin showed $B_S$-type behavior according to the classification of Higuchi [T. Higuchi et al., *Adv. Anal. Chem. Instrum.* (1965) 4:117-212] and Brewster [M E. Brewster et al. *Adv. Drug Delivery Rev.* (2007) 59:645-666] (FIG. 20). The API concentration first increased with increasing cyclodextrin concentration due to the complexation of the API with cyclodextrin molecules. After an initial increase in drug solubility, the maximum solubility of the complex was reached and the complex started to precipitate, indicating the formation of a less soluble inclusion complex (γ-CD inclusion complex). At the end of the plateau, the entire solid API has been consumed and further addition of API would result in depletion of API in the solution by complex formation and concomitant precipitation of the insoluble complex. 150 mM represents the solubility limit of γ-cyclodextrin in aqueous solution.

The binding constant (K) of the γ-CD inclusion complex was calculated from the initial straight line portion of the phase solubility diagram by linear regression, according to the following equation [T. Higuchi et al., *Adv. Anal. Chem. Instrum.* (1965) 4:117-212]:

$$K = \frac{\text{slope}}{\text{intercept} \times (1 - \text{slope})} = \quad \text{(Eq. 1)}$$

$$\frac{0.00131}{0.00000257 \times (1 - 0.00131)} M^{-1} = 510.4 M^{-1}$$

The binding constant of the γ-CD inclusion complex calculated according to equation (1) was 510.4 $M^{-1}$. The binding constant (K) is a measure of the affinity of the API to enter the relatively apolar cavity of the CD. The desired situation is to have sufficient affinity, such as to enhance the concentration of total dissolved drug, but still allow for dissociation of the complex followed by absorption of the API. A binding constant of 510.4 $M^{-1}$ in case of the γ-CD inclusion complex is in a good range and suggests that an oral solid dosage form with an increased dissolution rate should be feasible.

Example 28

In Vitro Dissolution Results

The in vitro dissolution studies performed in this work were conducted in a miniaturized system with 100 mL dissolution medium per experiment. In comparison to the 1000 mL vessels of the conventional USP apparatus the experimental set-up that was used here was scaled-down and simplified (magnetic stirring instead of paddles, room temperature instead of 37° C.). The dissolution experiments were performed under non-sink conditions (drug concentration>10% of the solubility value). Simulated gastric fluid (SGF) was prepared with 2 g/L NaCl and 1 g/L Triton® X-100 in 0.1 N HCl. The resulting measured pH of SGF was 1.2. Simulated fed state intestinal fluid (FeSSIF) was prepared as previously reported in Galia E. et al. (*Pharm. Res.* (1996) 13:S-262) and contained 15 mM sodium taurocholate, 3.75 mM lecithin and had a pH 5.0.

Oral absorption of a drug compound from a solid dosage form is dependent on dissolution rate and solubility. In the present work the in vitro dissolution of the γ-CD inclusion complex was compared to micronized powders of polymorph Form A, Form B and Form C. FIG. 21 presents the dissolution profiles measured in simulated gastric fluid (SGF) and FIG. 22 shows the dissolution profiles in simulated fed state intestinal fluid (FeSSIF). In both dissolution media the γ-CD inclusion complex behaves completely different compared to micronized powders of polymorph Form A, Form B and Form C. The γ-CD inclusion complex achieved a much higher initial concentration in SGF and FeSSIF which rapidly dropped in the first 60 min to a level which was comparable to polymorph C values. In case of the micronized powders of polymorphs the saturation solubility of the specific polymorphs was relatively rapidly achieved (≤30 min) and the dissolved drug contents remained unchanged until the end of the experiment (180 min). Changes of pH values in the dissolution test samples taken at different time points were not observed. The ranking of the different solid forms with respect to dissolution speed and maximum drug concentration achieved was identical in both media. The differences in the dissolution profiles in SGF and FeSSIF can be explained by the different composition of the two media since the dissolution generally depends on a variety of factors such as pH, surfactant, buffer capacity, ionic strength, etc. The ability of the γ-CD inclusion complex to form a supersaturated solution presents promising opportunities to increase the in vivo absorption and oral bioavailability compared to the crystalline pure phases of Form A, Form B and Form C.

To maintain the supersaturation promoted by the γ-CD inclusion complex the addition of specific precipitation inhibitors such as hydroxypropyl methylcellulose (HPMC), polyvinylpyrrolidone (PVP), etc. to the final dosage form can be beneficial. A prolongation of the supersaturated state can dramatically impact and improve in vivo absorption and bioavailability.

The invention claimed is:
1. A solid font of the compound of formula (I)

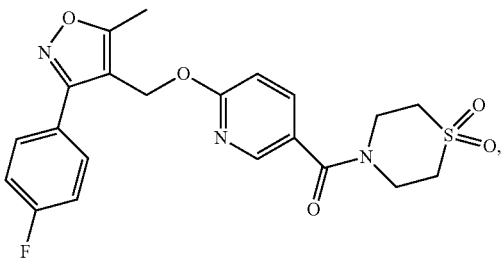

(I)

having an XRPD pattern comprising at least one XRPD peak in the range of angles of diffraction 2Theta of 10.3° to 13.3°, wherein the solid form is crystalline (1,1-dioxo-1$\lambda^6$-thiomorpholin-4-yl)-{6-[3-(4-fluoro-phenyl)-5-methyl-isoxazol-4-ylmethoxy]-pyridin-3-yl}-methanone in anhydrous polymorphic form C.

2. The compound of claim 1, comprising crystalline 1,1-dioxo-1$\lambda^6$-thiomorpholin-4-yl)-{6-[3-(4-fluoro-phenyl)-5-methyl-isoxazol-4-ylmethoxy]-pyridin-3-yl}-methasone in anhydrous polymorphic form C, having an XRPD diffraction pattern comprising XRPD peaks at angles of diffraction 2Theta of approximately 17.4°, 23.4°.

3. The compound of claim 1, having crystalline polymorphic form C, having the XRPD diffraction pattern of FIG. 3.

4. The compound of claim 1, comprising crystalline polymorphic form C, having the FTIR spectrum of FIG. 10.

5. The compound of claim 1, comprising crystalline polymorphic form C, having the Raman spectrum of FIG. 16.

6. The solid form of claim 1, having a purity of at least 90% (w/w).

7. A high-shear process for preparing a solid form of a compound of formula (I)

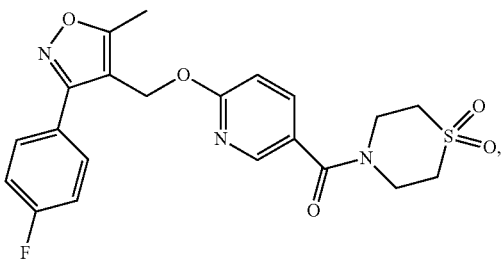

(I)

having an XRPD pattern comprising at least one XRPD peak in the range of angles of diffraction 2Theta of 103° to 13.3° comprising:

a) injecting a solution of an educt solid form of compound (I) in a solvent into a high-shear mixer having a rotor-stator system comprising an antisolvent;

b) agitating the rotor-stator system of the high-shear mixer to form a suspension; and c) physically separating the solid form from the suspension.

8. A pharmaceutical composition comprising a solid form of a compound of formula (I) the compound of formula (I)

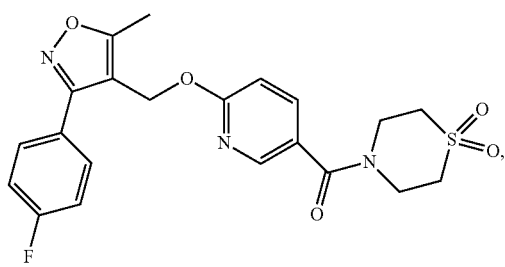

(I)

having an XRPD pattern comprising at least one XRPD peak in the range of angles of diffraction 2Theta of 103° to 13.3° and a pharmaceutically acceptable excipient, wherein the solid form is crystalline (1,1-dioxo-1$\lambda^6$-thiomorpholin-4-yl)-{6-[3-(4-fluoro-phenyl)-5-methyl-isoxazol-4-ylmethoxy]-pyridin-3-yl}-methanone in anhydrous polymorphic form C, wherein the pharmaceutical composition is administered in an administrative form selected from tablets, powders, and capsules.

* * * * *

UNITED STATES PATENT AND TRADEMARK OFFICE
CERTIFICATE OF CORRECTION

| | | |
|---|---|---|
| PATENT NO. | : 8,785,435 B2 | Page 1 of 1 |
| APPLICATION NO. | : 13/650159 | |
| DATED | : July 22, 2014 | |
| INVENTOR(S) | : Dott et al. | |

It is certified that error appears in the above-identified patent and that said Letters Patent is hereby corrected as shown below:

In the Claims

On column 35, line 2 of claim 1, should read:

-- A solid form of the compound of formula (I) --

Signed and Sealed this
Twenty-first Day of October, 2014

Michelle K. Lee
*Deputy Director of the United States Patent and Trademark Office*